United States Patent
Holland et al.

(10) Patent No.: US 10,500,227 B2
(45) Date of Patent: *Dec. 10, 2019

(54) BIOACTIVE GAS-ENCAPSULATED ECHOGENIC LIPOSOMES AND METHODS FOR TREATING CARDIOVASCULAR DISEASE

(71) Applicant: University of Cincinnati, Cincinnati, OH (US)

(72) Inventors: Christy Holland, Cincinnati, OH (US); Jason Raymond, Cincinnati, OH (US); Jonathan Sutton, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/957,705

(22) Filed: Dec. 3, 2015

(65) Prior Publication Data

US 2016/0250252 A1 Sep. 1, 2016

Related U.S. Application Data

(60) Provisional application No. 62/086,749, filed on Dec. 3, 2014.

(51) Int. Cl.
*A61K 41/00* (2006.01)
*A61K 9/127* (2006.01)
(Continued)

(52) U.S. Cl.
CPC .......... *A61K 33/00* (2013.01); *A61K 41/0028* (2013.01); *A61K 9/0019* (2013.01); *A61K 9/1271* (2013.01); *A61K 9/1278* (2013.01)

(58) Field of Classification Search
None
See application file for complete search history.

(56) References Cited

U.S. PATENT DOCUMENTS 5,585,112 A * 12/1996 Unger .................... A61K 9/127
264/4.1
5,837,221 A * 11/1998 Bernstein ........... A61K 49/0002
424/489

(Continued)

FOREIGN PATENT DOCUMENTS

WO WO 1986/004232 * 7/1986
WO WO 2014/026117 * 2/2014

OTHER PUBLICATIONS

JL Raymond, KJ Haworth, KB Bader, K RAdhakrishnan, JK Griffin, S-L Huang, DD McPherson, CK Holland. "Broadband Attenuation Measurements of Phospholipid-Shelled Ultrasound Contrast Agents." ULtrasound in Medicine and Biology, vol. 40 No. 2, 2014, pp. 410-421. (Year: 2014).*

(Continued)

*Primary Examiner* — Isaac Shomer
(74) *Attorney, Agent, or Firm* — Dinsmore & Shohl LLP

(57) ABSTRACT

Echogenic liposomes (ELIP) formulated with an at least partially pegylated phospholipid bi-layer shell, encapsulated nitric oxide, and encapsulated perfluorocarbon of the formula CxFy in a ratio of about 1:1 by volume, wherein X is greater than or equal to 3, are disclosed, along with methods for treating a patients suffering from cardiovascular disease by administering the ELIP at a site remote from the target diseased section, monitoring presence of the ELIP at the target diseased section, and administering ultrasound upon detection of presence such that bioactive NO is released at the target diseased section.

6 Claims, 10 Drawing Sheets

(51) Int. Cl.
  *A61K 33/00* (2006.01)
  *A61K 9/00* (2006.01)
  *A61K 47/69* (2017.01)
  *A61K 49/22* (2006.01)
  *G01N 33/50* (2006.01)

(56) References Cited

U.S. PATENT DOCUMENTS

| | | | | |
|---|---|---|---|---|
| 5,846,517 | A * | 12/1998 | Unger | A61B 5/411 |
| | | | | 424/9.52 |
| 6,146,657 | A | 11/2000 | Unger et al. | |
| 7,976,743 | B2 * | 7/2011 | Huang | A61K 9/127 |
| | | | | 264/4.1 |
| 2011/0144019 | A1 * | 6/2011 | Unemori | A61K 38/2221 |
| | | | | 514/12.7 |

OTHER PUBLICATIONS

JT Sutton, JL Raymond, MC Verleye, GJ Pyne-Geithman, CK Holland. "Pulsed ultrasound enhances the delivery of nitric oxide from bubble liposomes to ex vivo porcine carotid tissue." International Journal of Nanomedicine, vol. 9, pp. 4671-4683, available online Oct. 6, 2014. (Year: 2014).*

Y Endo-Takahashi, Y Negishi, Y Kato, R Suzuki, K Maruyama, Y Arannaki. "Efficient siRNA delivery using novel siRNA-loaded Bubble liposomes and ultrasound." International Journal of Pharmaceutics, vol. 422, 2012, pp. 504-509. (Year: 2012).*

* cited by examiner

A

B

BIOACTIVE GAS-ENCAPSULATED ECHOGENIC LIPOSOMES AND METHODS FOR TREATING CARDIOVASCULAR DISEASE

PRIORITY

This application claims benefit under 35 U.S.C. § 119(e) to U.S. provisional application No. 62/086,749, filed Dec. 3, 2014, the entire disclosure of which is incorporated herein by this reference.

GOVERNMENT LICENSE RIGHTS

The subject matter of this application was developed in part with government support under contract number R01 HL074002, awarded by the National Institute of Health. The government therefore has certain rights in the invention.

TECHNICAL FIELD

The subject matter of this application relates to gas-encapsulated echogenic liposomes for the diagnosis and treatment of cardiovascular disease.

BACKGROUND

Cardiovascular disease (CVD) is currently the leading cause of death and is predicted to be the number one cause of disability worldwide by 2030 (World Health Organization 2014). In the United States, approximately 1 of every 3 deaths in 2010 was due to CVD. Ischemic heart disease and stroke were the leading primary causes of premature death. The overall economic impact of CVD was estimated to be $445 billion annually in the U.S. (2010), and is expected to increase substantially in future decades. More effective diagnostic tools and therapies are necessary to limit the growing burden of CVD in the U.S. and worldwide, particularly the diseases which manifest in unwanted clotting within the arteries of the heart or brain.

A major contributor to acute cardiovascular events and sudden deaths is the development of atherosclerotic plaques, a progressive thickening of the arterial wall due to the accumulation of cholesterol. Rupture of atherosclerotic plaques can form thrombi that occlude blood flow, potentially leading to a life-threatening event. Thrombi occurring in the coronary artery can lead to a heart attack, and in cerebral arteries can lead to ischemic stroke.

The early detection and treatment of CVD is vital to assess the risk of vulnerable plaque leading to an acute cardiovascular event. However, screening for vulnerable atherosclerotic plaque using current imaging modalities poses specific challenges. Direct visualization using noninvasive imaging methods, e.g. carotid ultrasound, cardiovascular computed tomography, magnetic resonance imaging, and positron emission tomography, are preferable for early diagnosis of vulnerable atherosclerotic plaque in high-risk patients. For example, carotid ultrasound with measurement of the intima-media thickness within the artery wall offers a way to diagnose the extent of subclinical atherosclerotic vascular disease, assess risk, and may offer a means to identify disease progression and monitor the effectiveness of preventive therapies. The use of microbubble based ultrasound contrast agents as a complementary tool to enhance vascular ultrasound imaging, known as contrast-enhanced ultrasound imaging, is emerging as an important method in facilitating the detection and characterization of atherosclerotic disease.

The use of microbubbles as ultrasound contrast agents (UCAs) in vascular imaging is well established. Most commercially available UCAs consist of gas-filled microbubbles which have mean diameters between 1-5 µm and are encapsulated with a protein, polymer, or lipid shell. Albunex® (GE Healthcare) was the first UCA approved by the U.S. Food and Drug Administration and consisted of an air-filled microbubble encapsulated by an albumin shell. Second generation UCAs such as Optison® (GE Healthcare), Definity® (Lantheus Medical Imaging) and Lumason® (Bracco Diagnostics, Inc.) contain high-molecular-weight gases (e.g. $C_3F_8$ and $SF_6$ respectively), which have lower solubility in blood and thus increase the lifetime of the microbubbles in circulation. The low density and high compressibility of the gas core in UCAs enables efficient ultrasound scattering. Thus, the injected agents are acoustically active, or echogenic, and function as intravascular tracers which can be visualized using ultrasound.

In addition to traditional contrast-enhanced ultrasound imaging, there has been recent interest in advancing the applications of UCAs for molecular imaging of atherosclerosis. Molecular imaging techniques with targeted UCAs are being used increasingly for noninvasive diagnosis of inflammation, thrombus, and neovascularization. Targeted microbubble agents are also being developed for controlled drug-delivery applications and have been vigorously promoted for therapeutic applications in the treatment of CVD. Targeted UCAs are functionalized by engineering the gas-encapsulating shell to contain molecules that adhere to cells which express disease-specific markers (e.g., aminoacids) on the membrane. Phospholipid-shelled UCAs are of particular interest for this purpose, because they can be targeted to molecular components of disease by attaching specific ligands to the surface.

Phospholipid-shelled UCAs represent one type of UCA that is currently available for clinical use. The lipid molecules employed in the formulations are typically amphiphilic molecules which spontaneously form micelle structures that can encapsulate and stabilize a gas microbubble in an aqueous environment. The lipids are surface-active molecules (surfactants) which orient their hydrophilic polar groups outside towards the surrounding aqueous medium and their hydrophobic tails inside away from the water, stabilizing the microbubble and largely preventing the gas from escaping the encapsulation. Lipid-based ultrasound contrast agents such as Definity® and Lumason® (which was recently approved for clinical use in the U.S. but has been marketed as SonoVue® in Europe and Asia since 2001) are commercially available for diagnostic applications. MicroMarker® (VisualSonics, Toronto, Canada; Bracco Research SA, Geneva, Switzerland) and Targestar® (Targeson Inc., San Diego, Calif., USA) are examples of targeted phospholipid-shelled UCAs currently available for pre-clinical investigational use.

A more recent formulation in the broad category of phospholipid-shelled UCAs, known as echogenic liposomes (ELIP), has been developed which encapsulates both a gas and an aqueous phase (Alkan-Onyuksel et al. 1996; Huang et al. 2001). Standard liposomes are characterized by a phospholipid bilayer shell which encapsulates an aqueous compartment. ELIP are said to be echogenic because they contain a gas microbubble that is highly reflective to ultrasound waves at low intensities. The exact location of the entrapped gas pockets in ELIP has not been fully ascertained, and may be due to gas pockets stabilized by lipid monolayers within the liposome, or within the lipid bilayer shell. Various proposed schematics of echogenic liposomes have been put forth in the literature. Two possible models of an echogenic liposome (ELIP) with an outer phospholipid bilayer and a lipid monolayer shell surrounding a gas bubble are presented in FIG. 9A and FIG. 9B. The models are qualitatively similar, the only difference being the ratio of the total particle volume occupied by the internal gas bubble. With respect to mechanism of gas entrapment, previous studies have suggested that the freeze-drying procedure is key to the generation of defects in the lipid bilayers such that upon rehydration, they fuse and trap small amounts of gas. After reconstitution in an aqueous suspension, the phospholipid molecules are known to stabilize the gas core by imparting low surface tension and high mechanical stability.

At low pressure amplitudes, ELIP have been utilized as an UCA to enhance image quality. Further, at high ultrasound pressure amplitudes, the microbubbles can be forced to expand and may cause the liposome membrane to rupture, thereby releasing the encapsulated gas or drug for a potential therapeutic effect. ELIP are therefore known as theragnostic agents because they can be used for both diagnostic and therapeutic purposes.

ELIP formulations differ from current commercially available contrast agents primarily in size, shell material, and gas content. Previous studies have shown that ELIP range in size from 70 nm to several microns. ELIP formulations typically contain 3 or 4 phospholipid components and also include a small amount of cholesterol, which acts to increase membrane rigidity. The gas content can be air, which is more soluble in blood than high molecular weight gases. However, unlike commercially available UCAs, ELIP with optimized lipid formulations have been shown to be both echogenic and stable under physiologic conditions for tens of minutes. Compared to commercially available UCAs, ELIP are unique in that they can function as diagnostic imaging contrast agents and can also serve as therapeutic drug carriers.

Targetable drug-delivery systems represent a fast developing area of nanotechnology and are expected to have a dramatic impact on medicine in the future. Many nano-scale drug carriers, such as liposomes, micelles, and polymer nanocapsules, have been developed or are under development for encapsulation and delivery of therapeutic drugs. Liposomes are a convenient, biologically compatible vehicle for administration of poorly soluble drugs, and are among the first generation of nano-scale drug delivery systems to be approved for clinical use and known as "nanomedicines" (Moghimi et al. 2005).

Gregoriadis and Ryman (1971) were the first to report on the use of liposomes as drug carriers for directed delivery. The authors hypothesized that encapsulation of enzymes within the aqueous inner compartment of liposomes would aid in directing the payload to a particular tissue and alleviate some of the problems associated with immunological response to the proteins in circulation. They found that liposomes remain largely intact during circulation and are cleared by lysosomes in the liver (and to a lesser extent in the spleen). Since then, liposome based drug-delivery systems have been developed using chemotherapeutic agents for cancer therapy, thrombolytic agents, and genes, in addition to enzymes.

Most of the currently approved liposome formulations represent a basic form of nanomedicine involving a passive targeting and drug release process known as the enhanced permeability and retention (EPR) effect. This approach relies on extravasation and accumulation of the liposome-encapsulated drug at the target site, and is particularly suited for cancer therapy applications due to the enhanced vascular permeability of tumors compared with normal tissue. Because tumors are highly vascularized and often lack effective lymphatic drainage, liposomes tend to accumulate in tumors much more than they do in normal tissues, resulting in increased drug uptake in these regions. Although EPR is a rudimentary passive targeting method, it is a key reason liposomes are currently the most widely used drug nanocarrier in cancer therapy. To realize the drug delivery potential of liposomes for other applications fully, however, it is important to develop agents with an active triggering mechanism that allows the drug to be delivered in a more controlled fashion. Echogenic liposomes, by virtue of their ability to encapsulate gas as well as therapeutic drugs, offer such a possibility.

Recently, ultrasound has been investigated as a method to trigger enhanced drug delivery within the human vasculature. The potential of ultrasound to control drug delivery spatially and temporally in a non-invasive manner is broadly appealing. Ultrasound-mediated drug delivery (UMDD) has been demonstrated in a number of tissue beds, for example the blood-brain barrier, cardiac tissue, prostate, and large arteries.

Acoustic cavitation is one physical mechanism that is hypothesized to influence UMDD. Cavitation as used herein refers to nonlinear bubble activity that can occur near vessel walls within the vasculature upon ultrasound exposure, which can exert mechanical stress on nearby cells and junctions. Mechanical stress can disturb the barriers to drug delivery such as endothelial tight junctions or phospholipid membranes, via transient permeabilization. In vivo, cavitation can be nucleated at moderate acoustic pressure amplitudes (<0.5 MPa) by ultrasound contrast agents (UCAs).

Conventional strategies for studying ultrasound-mediated drug release and delivery in vitro and ex vivo involve various techniques, from optical to electrophysiological. Optical techniques, such as fluorescence or luminescence, rely on the native optical properties of the therapeutic, or conjugation of tracer molecules. Electrophysiological approaches, such as voltage-clamp techniques, directly assess the changes in membrane potential provoked during UMDD, but often require isolated cells cultured in vitro, where cellular processes can vary drastically from in vivo conditions. In vivo animal models of UMDD provide relevant bioeffect information, yet are costly and subject to considerable inter-subject variability. The ability to detect and monitor the response of intact, isolated vascular tissue in real time would constitute a significant advancement is UMDD.

Nitric Oxide (NO) is a gas molecule that dynamically modulates the physiological functions of the cardiovascular system, which include relaxation of vascular smooth muscle, inhibition of platelet aggregation, and regulation of immune responses. Because a reduced NO level has been implicated in the onset and progression of various disease states, NO is expected to provide therapeutic benefits in the treatment of cardiovascular diseases, such as essential hypertension, stroke, coronary artery disease, atherosclerosis, platelet aggregation after percutaneous transluminal coronary angioplasty, and ischemia/reperfusion injury. To date, pharmacologically active compounds that can release NO within the body, such as organic nitrates and sodium nitroprusside, have been used as therapeutic agents, but their efficacy is significantly limited by their rapid NO release, poor distribution to the target site, toxicity, and induction of tolerance.

Attenuation of nitric oxide production in the etiology of atherosclerosis progression and diabetic vascular disease further highlights the need for novel therapeutic nitric oxide modulation and delivery strategies. Effective delivery of bioactive NO to target cardiovascular tissue remains a compelling need in the art.

Isolated tissue bath perfusion systems have been used extensively to characterize contractility changes induced by a therapeutic in a variety of muscular tissue beds including gastric, peripheral vascular, and cardiovascular. In these systems, dose-dependent changes in active muscular tension can be characterized in response to vasorelaxing agents such as bradykinin, sodium nitropursside, nitroglycerine, and NO. Development of an isolated tissue bath model to investigate UMMD could provide relevant, real time quantitative data on the drug release and delivery profiles triggered by ultrasound.

SUMMARY

Accordingly, the instant disclosure provides novel specialized NO-loaded liposomes designed to exploit the benefits discovered upon intensive investigation of the properties and release profiles of liposomes comprising various gases, combinations of gases, and ratios of specific gas combinations. Various echogenic liposomes were formulated and properties and release profiles in cardiovascular tissue characterized to provide methods of treating cardiovascular tissue that exhibited superior and unexpected benefits in the delivery and safe release of bioactive gases from liposomes at target diseased cardiovascular tissue sites. The ELIPs provide both diagnostic and therapeutic benefit.

One embodiment provides methods for treating a patient suffering from cardiovascular disease. The method comprises: delivering a liposome comprising nitric oxide (NO) locally to a target diseased section of the patient's vasculature; and releasing the NO at the target diseased section, wherein the liposome comprises NO in a ratio of from about 1:1 to about 1:10 by volume with a perfluorocarbon.

According to another embodiment, an ex vivo method for assessing therapeutic suitability of a liposome comprising NO and a perfluorocarbon in a volume ratio is provided. The method comprises (i) administering the liposome to a segment of vasculature while exposing the section of vasculature to ultrasound; and (ii) simultaneously measuring at least one indicator of ex vivo vascular tone and at least one indicator of acoustic response.

Another embodiment is directed to methods of manufacturing an echogenic liposome effective for ultrasound-mediated drug release, the method comprising: providing a liposomal emulsion comprising phospholipids, injecting a volume ratio of nitric oxide and a perfluorocarbon of the formula CxFy into the liposomal emulsion; agitating the emulsion; adjusting the temperature of the liposome formulation to room temperature, without any step comprising freezing of the liposomal emulsion.

Methods of quantitatively assessing an agent or an amount of an agent for efficacy in ultrasound-mediated drug release are also provided. The methods comprise: providing a viable segment of arterial vasculature mounted in a physiological buffer solution; coupling the arterial segment to an isometric force transducer; infusing agent-loaded liposome into a lumen of the segment while exposing the arterial segment to ultrasound; and monitoring at least one indicator of vascular tone, wherein an agent or an amount of an agent is assessed as exhibiting efficacy if a decrease in vascular tone of the arterial segment is indicated.

Still other embodiments are directed to novel specialized echogenic liposomes comprising an at least partially pegylated phospholipid bi-layer shell, encapsulated nitric oxide, and encapsulated perfluorocarbon of the formula CxFy, wherein X is greater than or equal to 3, further wherein the volume of NO is equal to or less than the volume of CxFy.

All references (e.g., printed publications such as books, papers, patents, patent applications, catalogs, databases) are incorporated herein by reference. In the event of a conflict or inconsistency, the present specification, as modified by any amendments thereto, shall control.

These and other embodiments will be more clearly understood by reference to the detailed disclosure and accompanying figures.

DETAILED DESCRIPTION

Figure 1:
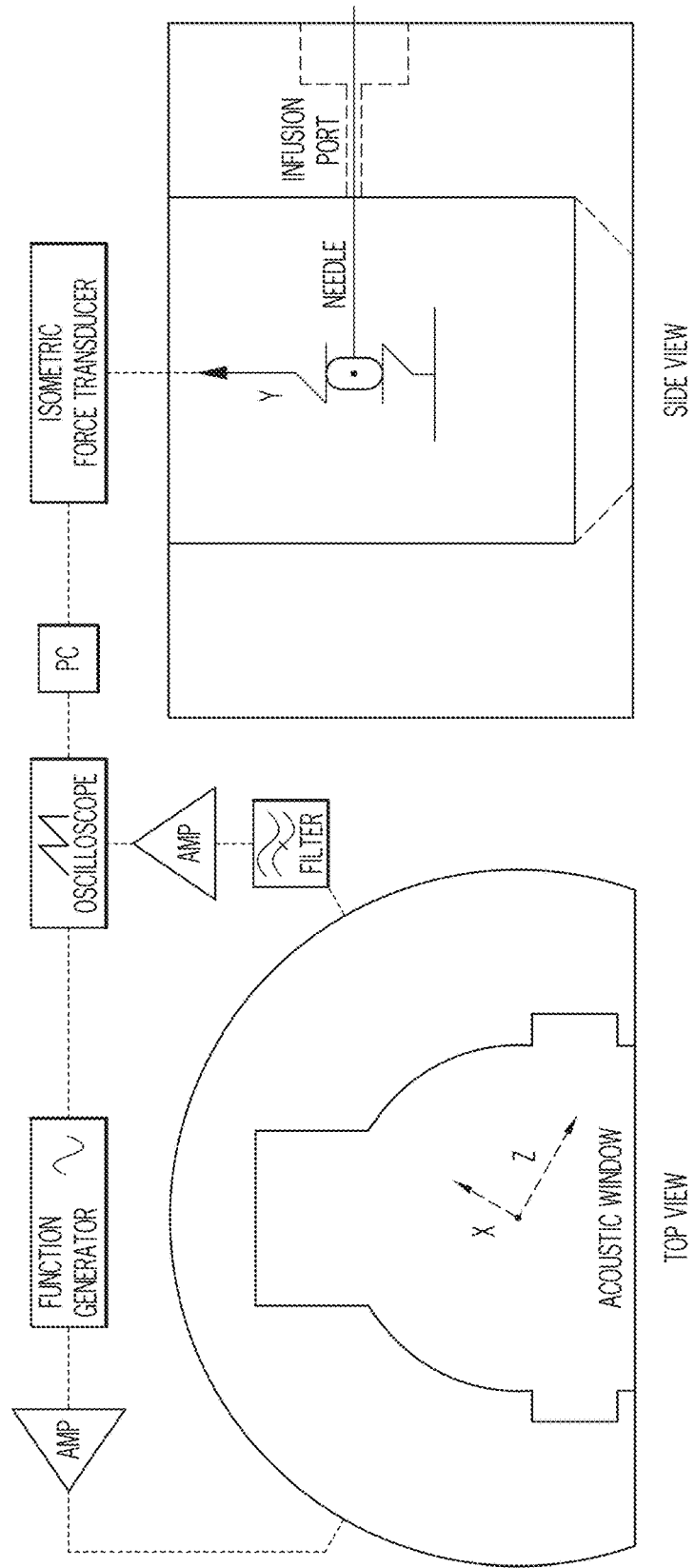
FIG. 1. Schematic representation of the electronic configuration of the disclosed ultrasound tissue bath system. Two submersible ultrasound transducers are coupled to the reservoir: a transmit transducer (1 MHz, 3% duty cycle) focuses on the lumen of the artery, while a second receive transducer (7 MHz) detects cavitation emissions from nitric oxide-loaded bubble liposomes perfused within the vessel lumen via a 26-gauge blunt injection needle.

The clinical goal of liposomes designed for diagnostics and therapy is to deliver a pharmaceutic to the injured area. Liposomes are substantially spherical, self-assembling closed structures formed of concentric lipid bilayers with an aqueous phase inside and between the lipid bilayers. Their ability to entrap different water-soluble compounds within the inner aqueous phase and lipophilic agents between liposomal bilayers upon self-assembly has made them useful for delivery of different kinds of drugs and for carrying diagnostic agents in a variety of imaging modalities. It is known that modification of the liposome shell with polyethylene glycol (PEG) enhances circulation time and a common strategy is to attach antibodies or different binding moieties to the liposomal surface to target specific affected areas. Such modified liposomes are currently under investigation for targeted intravascular drug delivery to cells and noncellular components (such as endothelial cells, subendothelial structures, and blood components) as the targeted sites for diagnosing and treating cardiac pathologies, including myocardial infarction, coronary thrombosis, and atherosclerosis.

Myocardial infarction (MI) results from occlusion of coronary arteries by thrombi. During the ischemic phase and following reperfusion, extensive myocardial cell death occurs within the ischemic zone. The use of liposomes for delivery of MRI contrast agents and the use of PEG to increase circulation time (substantially by avoiding recognition by liver cells), as well as the incorporation of binding partners such as antibody onto the liposome surface to achieve targeted delivery, are all strategies known in the art. Visualization of thrombi and thrombolytic therapy are now mostly based on liposome-based targeted delivery of contrast agents and thrombolytic drugs, such as the enzymes urokinase, streptokinase, and tissue plasminogen activator (tPA).

A recent approach utilizes acoustically reflective (echogenic) liposomes (ELIP) that can be targeted to promote site-specific acoustic enhancement of either imaging or drug delivery. Ultrasound-mediated drug delivery is a relatively new technique for enhancing the penetration of drugs into diseased tissue beds noninvasively. By encapsulating drugs into microsized and nanosized liposomes, the therapeutic can be shielded from degradation within the vasculature until delivery to a target site by ultrasound exposure. For example, doppler ultrasound treatment has been shown to result in earlier and more complete recanalization rates when tPA-loaded ELIP are co-administered. Echogenic liposomes have been used to further develop the targeted delivery of tPA and to investigate the effect of ultrasound exposure on thrombolytic efficacy. tPA is released from the nano-sized delivery complex when exposed to ultrasound.

Traditional in vitro or ex vivo techniques to quantify this delivery profile include optical approaches, cell culture, and electrophysiology. The present investigators have developed a system that permits characterization of the degree of nitric oxide (NO) delivery to viable porcine carotid tissue by direct measurement of ex vivo vascular tone. Specifically, an ex vivo perfusion model was adapted to assess ultrasound-mediated delivery of NO.

Previous studies have suggested that encapsulating NO with other gas components may improve the delivery profile of NO; however an effective bioactive mixture with sufficiently reduced diffusion has yet to be designed. Perfluorocarbons, which are already known and approved as conventional ultrasound contrast agents due to their low solubility in aqueous media and their low diffusivity compared to low-molecular weight, biologically inert gases such as $N_2$, were an initially thought to provide a possible solution, in particular since NO is soluble in certain perfluorcarbons such as OFP. Thus, the presence of OFP would theoretically delay diffusion of NO out of the liposome. However early studies concluded that the trade-off in lowered bioactivity versus preventing free diffusion was not desirable, as very large radius liposomes would be required in order to accommodate the required encapsulation volume determined in the prior art.

Based on the need to develop better acoustic techniques to diagnose and treat cardiovascular disease, an improved ELIP-based method of releasing the highly volatile, reactive compound nitric oxide locally within the vasculature was developed. One embodiment provides an ex vivo method for assessing therapeutic suitability of a liposome encapsulating NO and a perfluorocarbon in a volume ratio.

Embodiments of the invention provide systems and methods for quantitatively assessing an agent or an amount of an agent for efficacy in ultrasound-mediated drug release. The method comprises providing a viable segment of arterial vasculature, for example porcine carotid artery, mounted in a physiological buffer solution; coupling the arterial segment to an isometric force transducer; infusing agent-loaded liposome into a lumen of the segment while simultaneously exposing the arterial segment to ultrasound; The method comprises (i) administering the liposome to a segment of vasculature while exposing the section of vasculature to ultrasound; and (ii) simultaneously measuring at least one indicator of ex vivo vascular tone and at least one indicator of acoustic response. In specific embodiments the indicator of ex vivo vascular tone comprises measurement of arterial tension with a force transducer, and in very specific embodiments, comprises measurement of a passive cavitation emission. According to other specific embodiments the indicator of acoustic response is selected from echogenicity, nonlinear scattering, and combinations thereof. An agent or an amount of an agent is assessed as exhibiting efficacy if a decrease in vascular tone of the arterial segment is indicated. In specific embodiments, the arterial segment is exposed to between 1 and 30 MHz ultrasound at a peak-to-peak acoustic pressure of less than 0.5 MPa. In other specific embodiments, the peak-to-peak acoustic pressure is 0.34 MPa, and in very specific embodiments the arterial segment is exposed to 1-MHz ultrasound at a peak-to-peak acoustic pressure of 0.34 MPa.

The ultrasound energy may be provided as continuous or pulsed wave forms. In specific embodiments the ultrasound is pulsed. In other more specific embodiments, rest periods wherein no ultrasound is delivered to the target area for a measurable amount of time may be incorporated into either continuous or pulsed ultrasound delivery. The rest periods may be patterned or sporadic. Such rest periods may provide opportunity for reperfusion of the target treatment area.

In specific system and method embodiments, a confocal point is positioned at an axial center of a ring of the carotid artery and a calibrated 1-MHz transducer is confocally aligned with a 7.5 MHz passive cavitation detector using an ultrasonic pulser receiver such that the entire carotid artery segment is exposed to ultrasound while cavitation emissions are detected from the lumen.

By conducting experiments utilizing the inventive system, it was concluded that liposomes encapsulating NO alone, manufactured with conventional methods, are not acoustically stable and would not be physiologically efficacious, likely due to free diffusion of nitric oxide into the surrounding media. Hence, utilizing the guidance provided by the empirical data derived from investigating multiple lipid formulations and gas compositions in the novel bath system, liposomes particularly effective for the delivery of bioactive NO were developed.

Thus, other embodiments provide a novel echogenic liposomal shell that enhances shielding of the highly soluble NO from the external environment, and methods for manufacturing the novel echogenic liposomes.

In specific manufacturing embodiments, the methods comprise: providing a liposomal emulsion comprising phospholipids, injecting a volume ratio of nitric oxide and a perfluorocarbon of the formula $C_xF_y$ into the liposomal emulsion; agitating the emulsion; adjusting the temperature of the liposome formulation to room temperature. In methods known in the prior art, freezing of the liposomal emulsion was considered to be a necessary step for achieving encapsulation of gases and/or other agents at desired volumes. According to embodiments provided herein, freezing of the liposomal emulsion is avoided with retained or improved encapsulation. In specific embodiments, X≥3, and the ideal volume ratio of NO:$C_xF_y$ approaches 1:1 as X approaches 3. In very specific embodiments, X is 3, F is 8 ("OFP"), and the ratio of NO:OFP is 1:1. By eliminating the freezing step, complications and uncertainties inherent to the subsequently required thawing were eliminated. Further, it was observed that activation temperature had a measurable effect on the acoustic properties of the liposomes. Therefore, activation at room temperature is an important step and differs substantially from known methods in the art in which the liposome mixture is frozen and thawed just prior to use.

In one embodiment, solutions containing liposomes with varying ratios of nitric oxide to perfluorocarbon were injected directly into a viable carotid artery during exposure to ultrasound. This procedure permitted investigation of the tradeoff between acoustic response and efficacy by enabling simultaneous measurement of arterial vasodilation, a direct indicator of NO release, alongside echogenicity and nonlinear scattering, direct indicators of acoustic response. This system revealed that a 1:1 volume ratio of nitric oxide to perfluorocarbon was sufficient to permit robust acoustic response while retaining bioactivity commensurate with standard-of-care vasodilators.

According to specific embodiments, the lipid emulsion comprises phospholipids. In more specific embodiments the phospholipids consist of nonionic and/or anionic phospholipids. Cationic lipids may be minimized in order to avoid an affinity of the liposome to the anionic endothelial glycocalyx of the vascular walls, which decreases circulating time in vivo, which could necessitate local infusion and limit the clinical utility/applicability of the echogenic liposomes. Thus, according to specific embodiments, phospholipid emulsions with a minimum of cationic lipids, and without DOTAP are preferred.

According to very specific embodiments, the ELIP formulation comprises 1,2-dipalmitoyl-sn-glycero-3-phosphocholine (DPPC), L-α-phosphatidylcholine (EggPC), 1,2-dipalmitoyl-sn-glycero-3-phosphoethanolamine (DPPE), 1,2-dipalmitoyl-sn-glycero-3-phospho-(1'-rac-glycerol) (DPPG) and cholesterol (CH) in a molar ratio of 27:42:8:8:15. As shown in the examples, stability of this formulation was demonstrated at physiologic temperature. It was further demonstrated that this formulation yielded higher ultrasound attenuation than the 69:8:8:15 formulation first described by Huang et al. (2002).

According to another very specific embodiment, the ELIP is modified by incorporating a synthetic polymer compound to achieve a longer circulation time in vivo. Poly-(ethylene glycol) (PEG) is a hydrophilic compound with a flexible oligomer chain that can be incorporated on the liposome surface to act as a steric stabilizer and delay circulatory clearance by phagocytosis. PEG groups are referred to by numbers that indicate the average molecular weight, and are normally anchored to the lipid surface via a cross-linked lipid such as DPPE. In an exemplary pegylated ELIP, DPPE is replaced with DPPE-PEG2000. The pegylated ELIP formulation comprises DPPC, EggPC, 1,2-dipalmitoyl-sn-glycero-3-phosphoethanolamine-N-[methoxy(polyethylene glycol)-2000] (DPPE-PEG2000), DPPG, and CH in a molar ratio of 28:43:6:8:15. According to some embodiments, the liposome emulsion further comprises long-chain PEG, and short-chain PEG.

Size of the ELIP was also discovered to affect diffusion profile. It was discovered that acoustically driven diffusion is maximum for ELIP near the resonance size range of 1 μm. For ELIP that are initially slightly larger than resonance (1-2 μm), the oscillation amplitude increases during deflation and reaches a maximum amplitude when passing through resonance size. However, almost no deflation occurred for ELIP much larger than resonance (>2 μm). This resilience may be due to some of the energy being coupled into surface modes rather than volumetric oscillations, resulting in lower dilatation rates overall. These observations suggest that either (a) the size distribution or (b) the frequency of insonation can be adjusted to achieve the desired gas release profile from a population of ELIP. Practically, it is much easier to adjust the insonation frequency. However, a threshold was identified with respect to the dilatation rate below which an observable change in radius due to acoustically driven diffusion was unlikely for the 6 MHz acoustic tone bursts used in this study. Assuming monofrequency oscillations, the dilatation rate scales directly with the amplitude of radial oscillations, which is maximum for bubbles near resonance. However, the dilatation rate also scales directly with the angular frequency of the driving acoustic pressure wave. Operating at a lower frequency implies that larger amplitude oscillations would need to be obtained in order to promote acoustically driven diffusion. For larger amplitude oscillations, the maximum expansion ratio becomes correspondingly large and for expansion ratios exceeding about 2, inertial collapse is more likely. In this regime, rapid fragmentation may play a more significant role and this may impose a limitation on the lowest frequency suitable to promote acoustically driven diffusion if inertial cavitation is to be avoided.

The novel liposomal emulsion developed according to the guidance disclosed above may then be loaded with gas components to provide novel echogenic liposomes. For purposes of treating a subject suffering from cardiovascular disease, echogenic liposomes are formulated into an intra venous (IV) composition and injected or otherwise administered to the subject at a site remote from the target treatment area, for example diseased cardiovascular tissue. In one specific embodiment, the target treatment area is monitored for presence of the echogenic liposomes and upon detection of presence acoustic energy is applied sufficient to cause inertial or non-inertial cavitation depending on the clinical goal.

Preparation of liposomes into pharmaceutical-grade compositions formulated for IV administration is known in the art. In particular, Toh et al. "Liposomes as sterile preparations and limitations of sterilization techniques in liposomal manufacturing" Asian Journal of Pharmaceutical Sciences, Volume 8, Issue 2, April 2013, Pages 88-95, provides guidance for formulation of IV compositions of liposomes of the sizes disclosed herein. The entire disclosure of Toh et al. is incorporated herein by this reference.

The following Examples are set forth to illustrate particular embodiments of the invention and should not be construed as limiting the full scope of the invention as defined by the claims and understood by a person of skill in the art.

EXAMPLES

Example 1

This Example illustrates development of a tissue bath system model

Tissue Bath System

Figure 2:
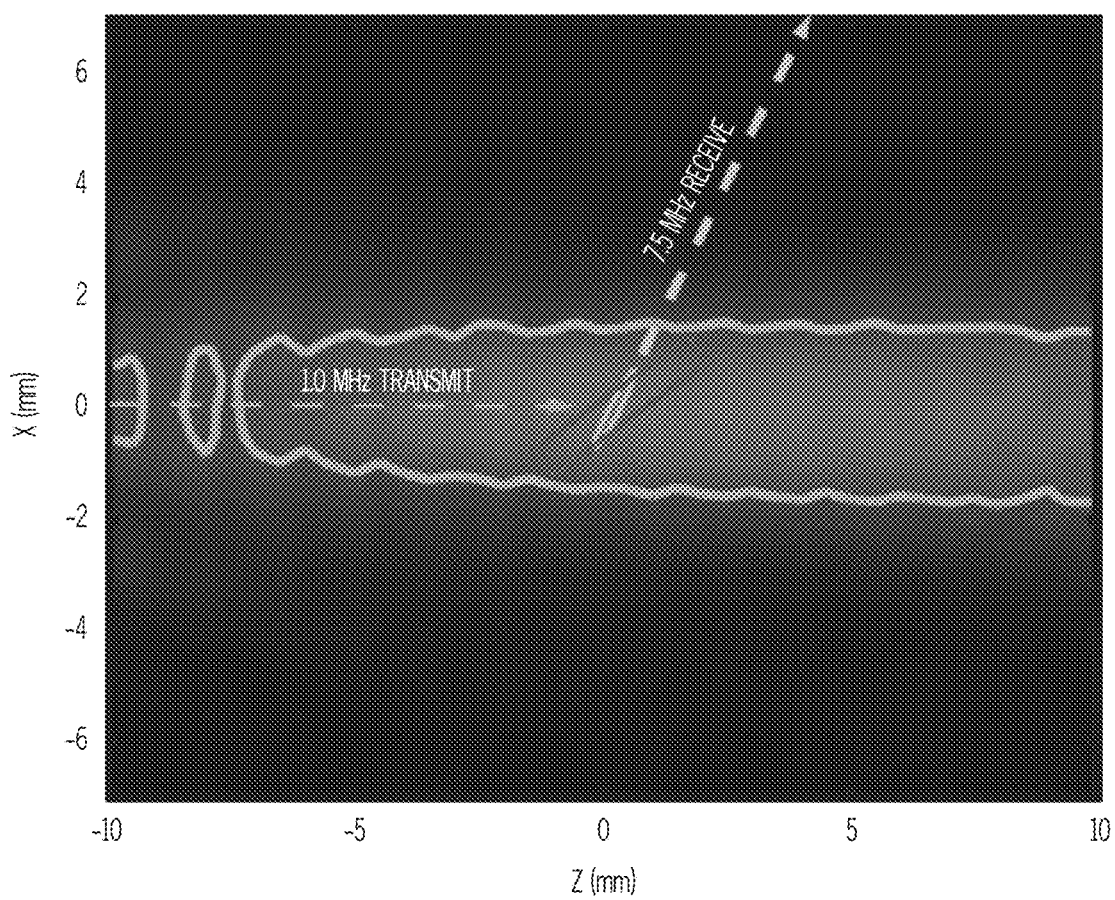
FIG. 2. Illustration of in situ ultrasound beam profiles of the 1 MHz and 7.5 MHz transducers. The −3 dB contours of the transmit field and receive sensitivity are depicted, along with the anticipated location of the artery (box).

Porcine carotid arteries were obtained post-mortem from young Yorkshire pigs according to a protocol approved by the Institutional Animal Care and Use Committee at the University of Cincinnati. Pigs were initially anesthetized with intravenous ketamine (30 mg/kg), followed by pentobarbital (35 mg/kg) for deep surgical anesthesia. Prior to artery excision, the animals were euthanized with saturated KCl solution (approximate concentration of KCl in vivo was 0.18 M). Segments of porcine carotid tissue were harvested immediately following sacrifice and stored in ice-cold, oxygenated Krebs-Henseleit buffer until use (NaCl: 115.9 mM; Kl: 5.4 mM; $MgSO_4$-$7H_2O$: 1.2 mM; $NaHCO_3$: 25 mM; d-glucose: 11.1 mM; $NaH_2PO_4$: 0.5 mM). The tissue was dissected free of loose adventitial and connective tissue and segmented into rings (mean ring length: 4.00 mm [S.D. 0.05 mm]; mean wet ring weight: 20.5 mg [S.D. 2.6 mg]). Each segment was mounted on two rigid, stainless-steel wires. The bottom wire was fixed to the tissue bath, and the top wire was coupled to an isometric force transducer (Radnoti LLC; Monrovia, USA) for measurement of arterial tension. The electronic configuration is depicted in FIG. 2. The tension signal was sampled digitally at 20 Hz (LabChart 6; AD Instruments, Colorado Springs USA and saved to a PC for post-processing. The carotid segment was submerged in a custom reservoir filled with KHB maintained at physiologic temperature with continuous bubbling of a 95%)2/5% $CO_2$ gas mixture to maintain physiologic pH (Range: 7.35-7.45).

Following the mounting of the artery and submersion in physiologic KHB, healthy arteries underwent a brief contraction and relaxation cycle. Artery rings not exhibiting this behavior were deemed unfit for experimentation and discarded. Healthy arteries consistently responded to pre-contraction with 50 mM Kl-doped KHB, however the extent of pre-contraction was variable (Range: 200-330 mN).

Prior to treatment, the arterial ring was pre-stretched to relieve the passive elastic component of arterial tension in a manner similar to that described by Herlihy and Murphy. Briefly, the artery was stretched incrementally by translating the force transducer with a micropositioning stage. The artery was contracted to steady state by perfusion with KHB containing 50 mM KCl after each increment. Following a KHB wash, this process was repeated until a maximum KCl contraction was achieved. The maximum contraction tension was determined to be 75 mN. Thus, subsequent rings were manually pre-stretched to this basal tension upon mounting.

Bubble liposomes containing octafluoropropane ("OFP" or "$C_3F_8$") were manufactured according to Endo Takahashi et al. ("Efficient siRNA delivery using novel siRNA-loaded Bubble liposomes and ultrasound" *Int J Pharm.* 2012 Jan. 17; 422(1-2):504-9, the entire disclosure of which is incorporated herein by this reference) for bubble liposomes. This liposomal formulation comprised dipalmitoylphosphatidylholine (DPPC), N-[1-(2,3-Dioleoyloxy)propyl]-N,N,N-trimethylammonium (DOTAP), polyethylene glycol (PEG) 2000, and PEG 750 in a 79:15:3:3 molar ratio. After manufacturing, 1 mL (1 mg lipid) of the liposomal emulsion was pipetted into glass vials, which were evacuated of headspace air with a laboratory vacuum, and stored at 4° C. until use. Immediately prior to use, vials were warmed to room temperature and 2.5 mL of gas was injected into the vial headspace through a rubber septum. For nitric oxide-loaded bubble liposomes (NOBLs) this gas consisted of a 50:50 volume ratio of NO gas and OFP gas. To assess the effect of cavitation on vasorelaxation, OFP-only bubble liposomes (OFPBL) were also manufactured by injecting 2.5 mL OFP gas. Following this step, the vial was mechanically amalgamated by shaking vigorously for 45 seconds. The amalgamation step heated the emulsion slightly, so the vial was allowed to equilibrate to room temperature. Immediately prior to experimental use, 500 ul of the liposomal emulsion was diluted into oxygenated ($pO_2$: 722 mmHg), room temperature KHB to a final concentration of 0.05 mg lipid/mL for infusion into the system.

A sample of the NOBL suspension was diluted (1:1000; v/v) into room temperature, aerated phosphate-buffered saline (Sigma-Aldrich) and the size distribution was measured using an impedance-based particle sizer (Multisizer 4, 30 µm aperture; Beckman Coulter, Brea, Calif., USA). Each measurement analyzed 100 µL of the diluted sample through a 30 µm aperture over 30 seconds. Each measurement produced a number density histogram, corrected for the dilution, with bins logarithmically spaced between 0.6 µm and 18 µm. This histogram was transformed into a volume-weighted distribution for further analysis. The results from three measurements, each using a fresh vial of NOBLs, were averaged to produce a final volume-weighted size distribution.

The frequency-dependent attenuation coefficient, α(f) in dB/cm, was determined using a broadband substitution technique, the components of which were described previously in Raymond et al. ("Broadband attenuation measurements of phospholipid-shelled ultrasound contrast agents" *Ultrasound Med Biol*. 2014; 2(40):410-421, the entire disclosure of which is incorporated herein in its entirety by this reference). Briefly, NOBLs were diluted (1:500) into a reservoir containing aerated phosphate-buffered saline, stirred, and allowed to flow by gravity into a sample chamber with acoustically transparent polycarbonate film windows (CLINIcell, Mabio, Tourcoing, France). The reservoir, sample chamber, and transducers were mounted in a test tank filled with distilled water maintained at 37° C.±0.5° C. using a circulating water bath (Neslab EX, Newington, N.H., USA). A pair of broadband transducers (PI-20, Olympus NDT, Waltham, Mass., USA) was used to acquire the through-transmission spectrum over the frequency range of 1-30 MHz (31 KPa peak negative pulse pressure; 33 dB dynamic range). The attenuation spectrum was computed from the received amplitude spectra in the absence (diluent alone) and presence of the bubble liposomes, respectively. Acoustic attenuation measurements were made in triplicate and a separate vial of NOBLs was used for each measurement.

Hemoglobin

The short half-life (<1 second) of NO in the presence of hemoglobin and oxygen in vivo limits the spatial extent over which NO can be effective as a signaling molecule. In order to mimic the in vivo milieu more closely and to quench nonencapsulated NO, 1 g/L hemoglobin (porcine, Sigma-Aldrich) was added to the reservoir prior to each treatment. Hemoglobin concentrations greater than 1 g/L produced a negligible decrease in vasorelaxation during NOBL+KHB infusions (FIG. 2) and occasionally caused vasospasmic contractions. Thus, 1 g/L hemoglobin was used in all subsequent treatments.

Ultrasound Exposure and Cavitation Detection

To reveal the mechanism of ultrasound-mediated drug release and delivery of NO to vascular tissue, two ultrasound transducers were coupled to the tissue bath reservoir. One transducer was used to deliver pulsed ultrasound to nucleate cavitation from the liposomes and a second transducer was used to monitor the acoustic emissions passively for evidence of acoustic cavitation. The experimental configuration is depicted in FIG. 1. Prior to each experiment, a calibrated 1 MHz therapy transducer (Olympus Panametrics, Waltham, Mass., USA) was aligned confocally with a 7.5 MHz passive cavitation detector (PCD; Olympus Panametrics) using an ultrasonic pulser receiver (5077PR; Olympus NDT). The confocal point was positioned in the axial center of the carotid ring using a three-axis translation stage (Newport 423, Irvine, Calif., USA). This geometry was chosen to ensure that the ultrasound therapy field encompassed the entire carotid artery, while cavitation emissions were detected primarily from the lumen. During experimental treatment, a function generator (Agilent Technologies, Santa Clara, Calif., USA) supplied a sinusoidal signal (30 cycles, 100 Hz pulse repetition frequency) that was amplified (750A250; Amplifier Research, Souderton, Pa., USA) and used to drive the 1 MHz therapy transducer. Acoustic scattering within the tissue bath reservoir affected the beam profile slightly. Therefore, an in situ pressure field calibration was performed in the absence of the artery ring and wires (FIG. 2).

Figure 3:
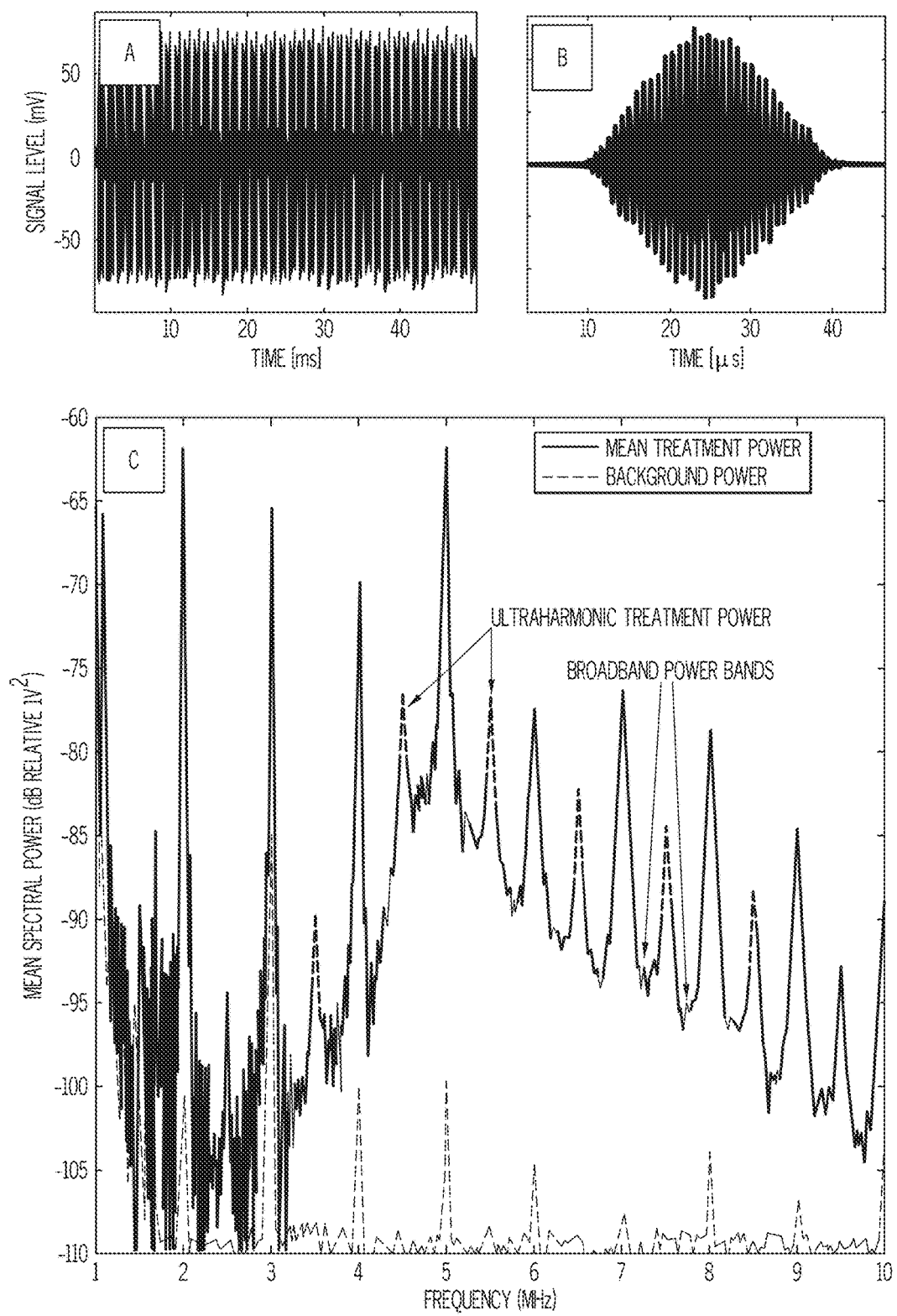
FIG. 3. Graphical representation of the signal processing technique used to assess cavitation emissions detected by the single element passive cavitation detector. 3A) Scattered pulses detected by the passive cavitation detector were filtered (1 MHz high pass filter), amplified (10×), digitized, and saved to a PC in sequence mode. 3B) Individual pulses were windowed in the time domain, and then transformed into the frequency domain. 3C) Ultraharmonic and broadband components of the power spectrum were quantified, and served as indicators of stable and inertial cavitation, respectively.

During ultrasound exposure, acoustic emissions were detected by the PCD, high-pass filtered (1 MHz high-pass, #07766 TTE, Los Angeles, Calif., USA), amplified (10×, Model 5185, Signal Recovery, Oak Ridge, Tenn., USA), and sampled at 20 MHz with an oscilloscope (LeCroy Model LT372, Chestnut Ridge, N.Y., USA). Sequences of 128 voltage time traces were saved to a PC for post-processing (FIG. 3A). To enable cavitation detection spaced more consistently in time, one of every four pulses was saved. The traces were analyzed using a custom MatLab (The Mathworks Inc, Natick, Mass., USA) script to extract spectral information associated with specific modes of bubble activity. A window (Blackman window, MatLab) was applied to each scattered pulse (FIG. 3B) and transformed into the frequency domain. Each frequency spectrum was scaled to account for the energy lost due to windowing. A frequency domain comb filter was applied to the power spectrum (FIG. 3C) to extract the ultraharmonic (100 kHz bands at odd multiples of 500 kHz) and broadband (50 kHz bands between harmonic and ultraharmonic frequencies) components of the spectrum. The energy contained in the ultraharmonic and broadband signals was associated with stable and inertial cavitation, respectively. This process is depicted graphically in FIG. 3.

Ultrasound parameters were chosen to promote stable cavitation nucleated by the NOBLs within the lumen of the arterial ring over the 55-second treatment. A 30-cycle therapy pulse was chosen to minimize standing waves in the reservoir. To determine the optimal acoustic pressure to promote stable cavitation, a dose-escalation approach was employed. An artery was mounted within the reservoir filled with oxygenated KHB containing 1 g/L hemoglobin. NOBL infusions (0.2 mL/min) with concurrent ultrasound exposure and cavitation detection were performed serially. Between each treatment, the reservoir was flushed with fresh hemoglobin-doped KHB and the acoustic pressure increased incrementally. This process was repeated at peak-to-peak acoustic pressure amplitudes ranging from 0 MPa to 0.38 MPa. The peak-to-peak acoustic pressure amplitude that promoted maximal ultraharmonic energy over the 50-second ultrasound exposure (0.34 MPa) was chosen for all subsequent exposures.

Figure 4:
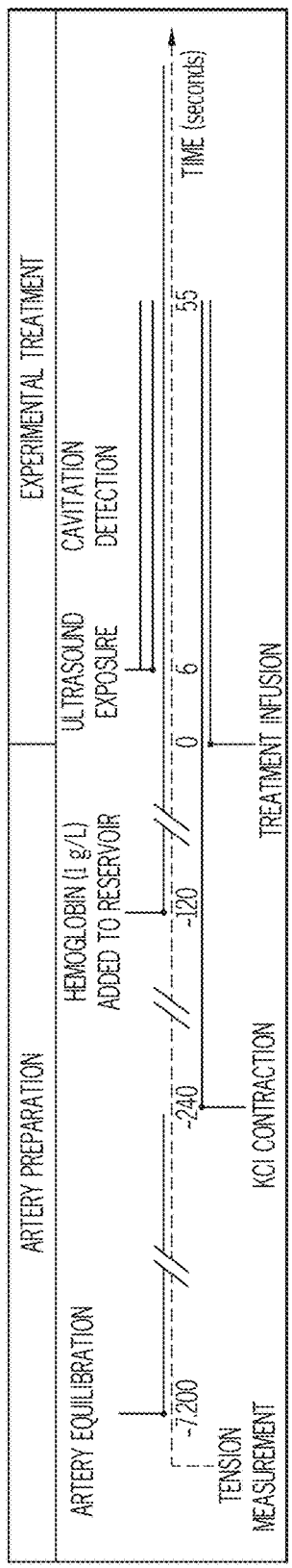
FIG. 4. Graphical timeline of procedures performed during a typical experimental exposure. Repeated measurements were made in series following 35 mM potassium chloride washes, followed by tension equilibration.

During treatment, the lumen of each artery was infused for 55 seconds with randomized combinations of buffer alone, buffer with NOBLs, or buffer with 12 μM sodium nitroprusside (Sigma-Aldrich) using a 24-gauge blunt hypodermic needle connected to a syringe pump (KD Scientific, #23; Canning Vale, Australia). After 5 seconds of infusion, ultrasound or sham exposure and cavitation detection commenced. This experimental procedure is diagrammed in FIG. 4.

Tension Analysis

Arterial ring tension was analyzed using a custom MatLab script. Each tension curve was normalized to the maximum tension produced by 50 mM KCl KHB using Equation 1:

$$\% \text{ Relaxation} = \frac{T(t) - T_{MAX}}{T_{MAX} - T_{BASAL}} \quad (1)$$

where $T_{MAX}$ is the initial tension produced by KCl contraction, $T(t)$ is the arterial tension as a function of time, and $T_{BASAL}$ is the basal tension after manual stretching (75 mN). A representative tension curve for each treatment is given in FIG. 5. For each treatment, the minimum value percent relaxation, i.e., maximal relaxation was used to compare across treatment groups. This metric has been used previously to compare treatments in NO-related vascular tension studies.

Statistical Analyses

In general, the mean and standard deviation of each data set was reported. Statistical analyses were performed using MatLab (Statistical Toolbox). Normal distributions were confirmed using Lilliefors test, with a threshold P-value of 0.05. Differences in means between treatment groups were analyzed using a one-way unbalanced analysis of variance. P-values less than 0.05 were considered to be statistically significant. Subsequently, pairwise comparisons with a Bonferroni correction were performed to compare across individual treatments to minimize the family-wise error rate for multiple comparisons.

Linear regression was performed to test for a correlation between maximal relaxation and (a) wet tissue weight, (b) 35 mM KCl tension, and (c) cavitation energy. A one-way unbalanced analysis of variance was used to test for significant correlations. For these tests, the P-value, f-statistic (Fstat), and degrees of freedom (df) are reported. Spearman's rank correlation coefficients (ρ) were computed to test for monotonic statistical relationships. The null hypothesis of no correlation was tested to produce a P-value; values below 0.05 were considered to be statistically significant.

Results

Liposome Characterization

Figure 6:
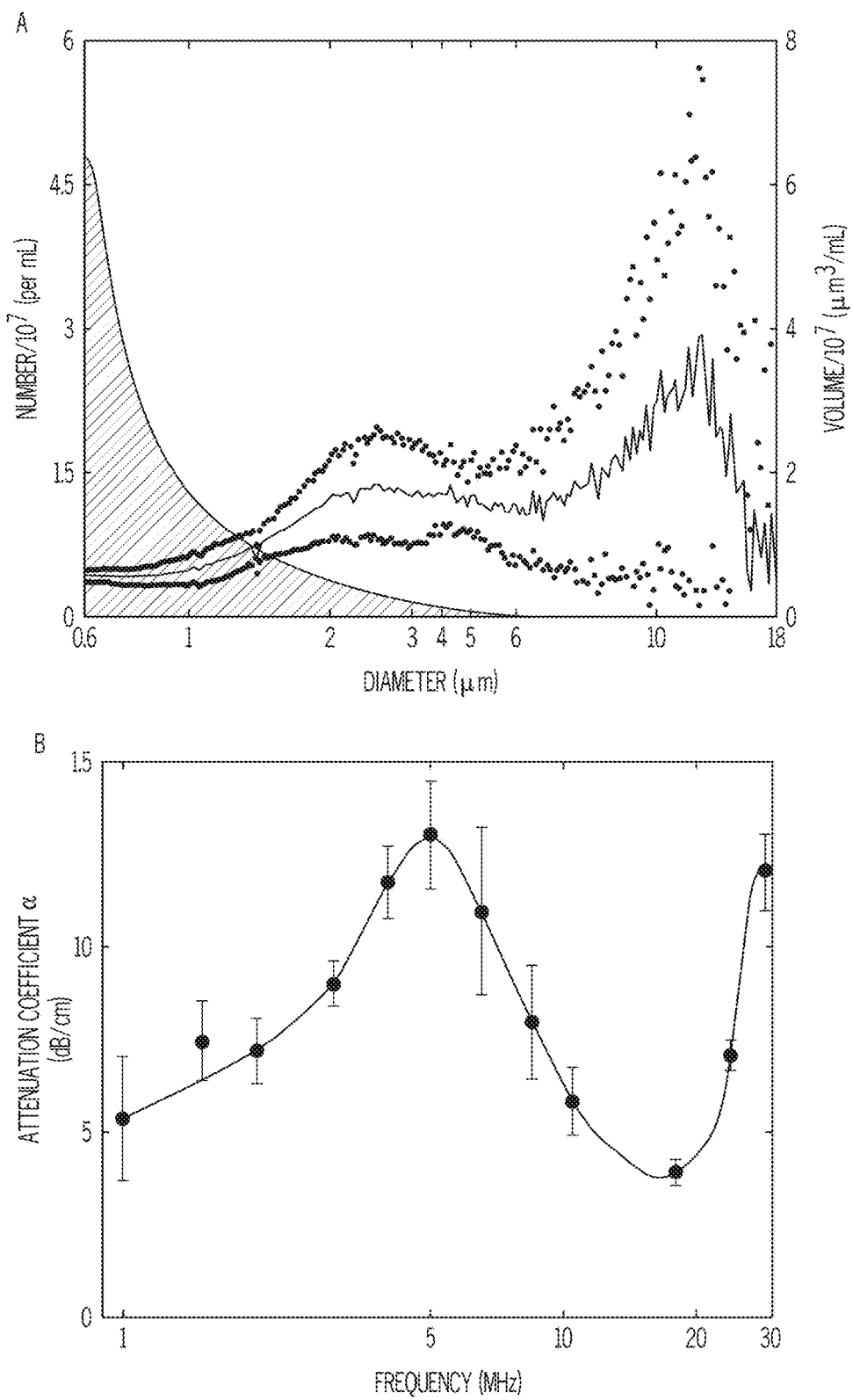
FIG. 6. 6A) Shows size distribution (n=3) of the NOBLs, weighted by volume (black) and number density (gray). Dots indicate one standard deviation. 6B) Shows acoustic attenuation as a function of frequency.

As depicted in FIG. 6A, NOBLs had a broad, bimodal volume-weighted size distribution, ranging in diameter from approximately 1.5 μm to 15 μm. The peak volume density occurred at a diameter of 2.5 μm. A separate population of particles existed at 11 μm, diminishing in diameter above 15 μm. FIG. 6B shows the measured attenuation coefficient as a function of frequency for NOBLs (n=3). NOBLs attenuated ultrasound across the 33 dB bandwidth of the system (1-30 MHz). A strong, broad resonance peak (α=13.0 dB/cm) was observed at 5 MHz. A second resonance peak (α=12.3 dB/cm) was observed near 28 MHz. NOBLs attenuated weakly between these two frequencies.

Cavitation

Figure 7:
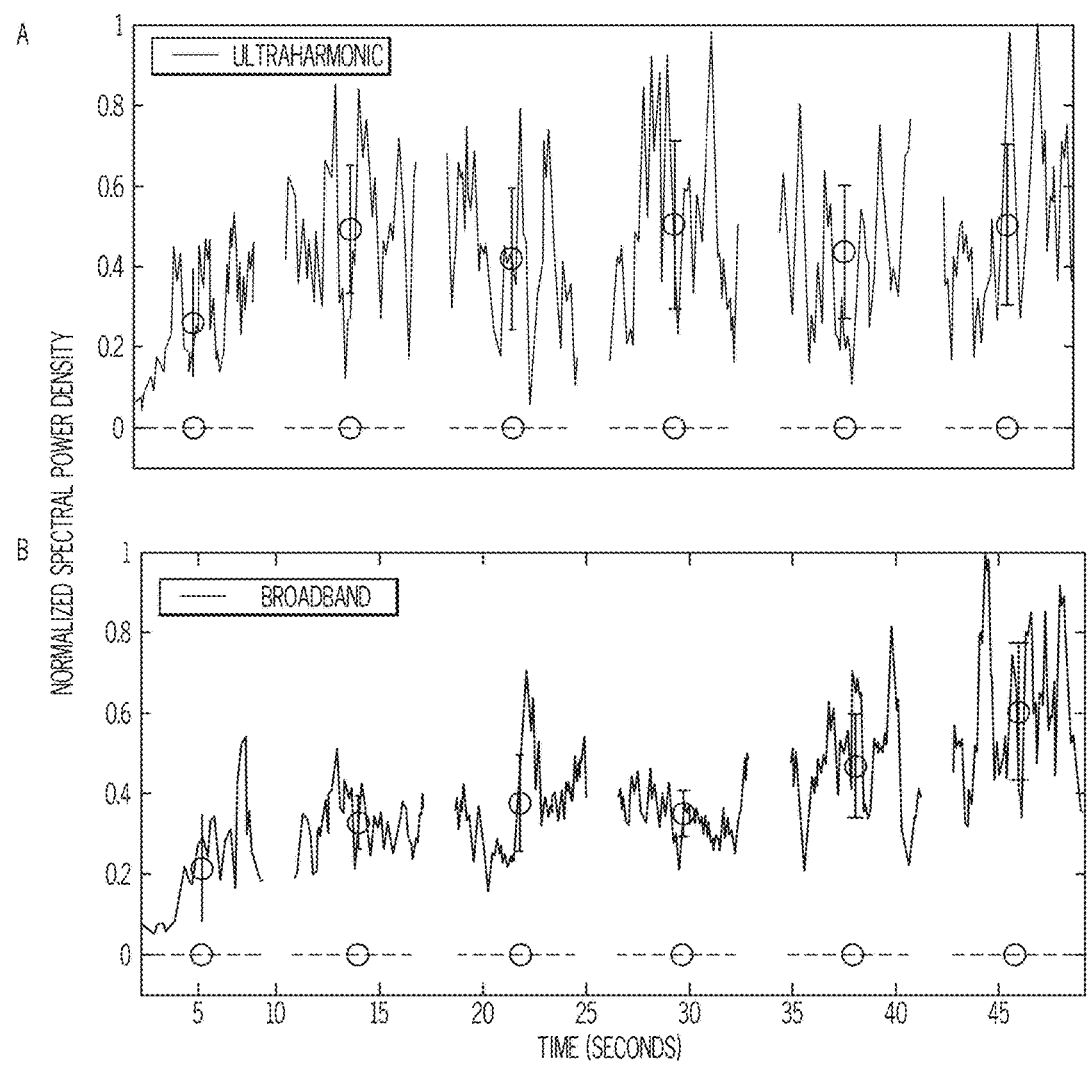
FIG. 7. Sets forth a spectral analysis of scattered acoustic signal from NOBLs. Averaged spectrum of detected cavitation emissions across a 50-second ultrasound exposure during NOBL infusion into the lumen of a carotid artery (solid), compared to spectral emission from sham ultrasound exposures (buffer+ultrasound alone, dotted). 7A) Ultraharmonic (eg, 3f/2, 5f/2) and 7B) broadband frequency components of the transmitted fundamental frequency (f, 1 MHz) were consistently observed, indicating strong, persistent nonlinear bubble activity. Black circles indicate the mean of the local data group, bars indicate±one standard deviation.

In general, ultraharmonic and broadband acoustic emissions within the arterial lumen persisted throughout the 50-second exposures in all eight ultrasound-treated arteries. FIGS. 7A and 7B show representative traces of the ultraharmonic and broadband acoustic power detected by the PCD as a function of time. A representative spectrum, averaged over the 55-second treatment, is depicted in FIG. 3C. Ultraharmonic energy was typically strong, yet variable, during the first few seconds of ultrasound exposure, and remained steady for the duration of the 50-second exposure. Within the NOBL+ultrasound treatment group, no correlation was observed between maximal relaxation and the average spectral emissions (ultraharmonic, ρ=−0.45, P=0.21; harmonic, ρ=−0.46, P=0.25; broadband, ρ=−0.50, P=0.21).

Vasorelaxation

Figure 8:
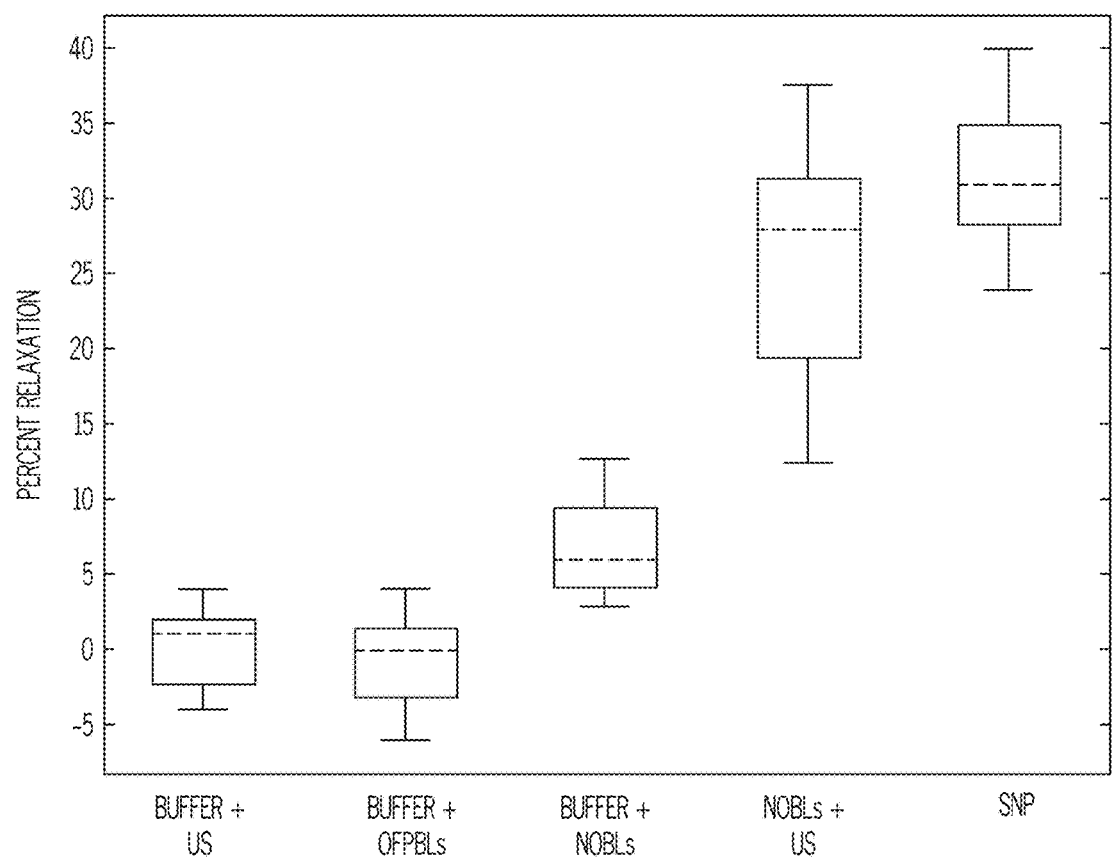
FIG. 8. Sets forth a graphical representation of carotid artery vasorelaxation as a function of treatment. Data means are indicated by horizontal dotted lines and boxes indicate the 25th and 75th percentiles. The range of adjacent data is indicated by error bars. Seven arterial rings from seven pigs were used for all treatments. Statistically significant differences in data means (P<0.05) were observed between all data sets except buffer+US/buffer+octafluoropropane bubble liposome (OFPBL) and NOBLs+US/SNP.
Figure 9:
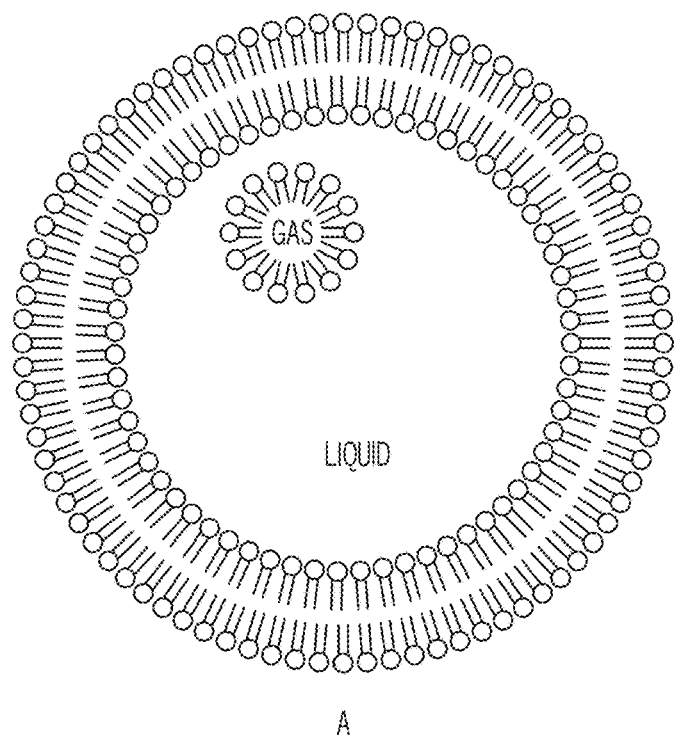
FIG. 9. Two possible schematic models of an echogenic liposome (ELIP) with an outer phospholipid bilayer and a lipid monolayer shell surrounding a gas bubble (not to scale). 9A) A gas bubble in the internal aqueous compartment of the liposome occupies a fraction of the total particle volume. 9B) The gas bubble volume is nearly equivalent to the particle volume and the aqueous compartment is limited to the hydration layer between the hydrophilic phospholipid head groups.
Figure 9:
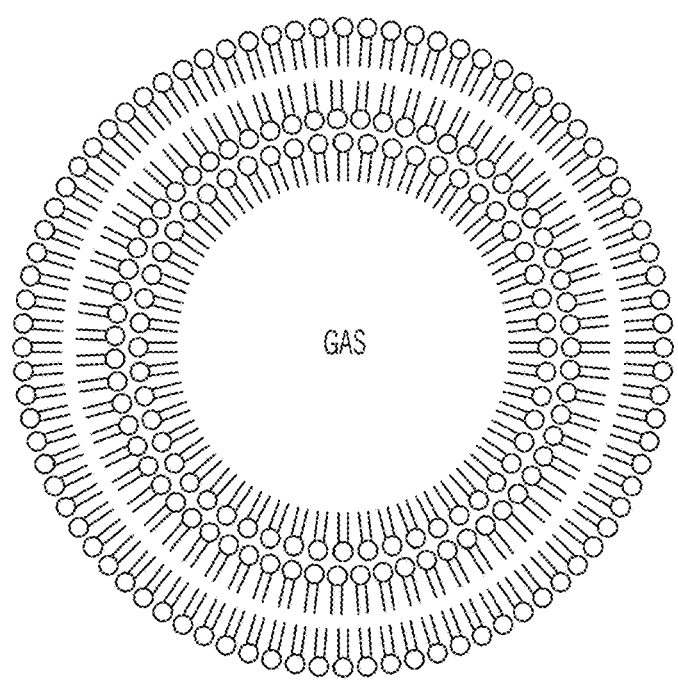

Seven carotid rings each from seven separate pigs were exposed to each experimental treatment, as shown in FIG. 8. Carotid rings relaxed in response to treatments in a characteristic manner, ie, a sharp tension decrease followed by steady restoration to the tension level induced by 35 mM KCl precontraction. Neither the order of treatment nor the time post-excision from the animal (ρ=−0.45, P=0.21) resulted in an apparent trend in maximal relaxation. Relaxation after 12 μM sodium nitroprusside infusions was significantly stronger (32%±5%) than NOBL infusions (P<0.01, Fstat=104.15, df=13) and sham control treatments, which consisted of buffer and NOBLs (7%±3%), buffer and ultrasound (1%±2%), or OFP bubble liposomes and ultrasound exposure (2%±1%). Arterial rings exposed to NOBLs+ultrasound experienced strong maximal relaxation (31%±8%) that was significantly greater than buffer and NOBLs (P<0.001, Fstat=29.01, df=13) and statistically identical to treatment with 12 μM sodium nitroprusside (P=0.18, Fstat=2.06, df=13). Across all experimental samples, no correlation was observed between the maximal relaxation and precontraction tension (P=0.82, Fstat=0.05, df=21) or wet tissue weight (P=0.33, Fstat=0.98, df=21).

Liposome Characterization

The characteristics of NOBLs can be compared directly with previously reported data on OFP-loaded bubble liposomes manufactured using similar methods. Endo-Takahashi et al. reported a volume-weighted size distribution peak at 749 nm with a significant volume-weighted population greater than 4 μm. The bubble liposomes of Endo-Takahashi et al. containing only OFP, are smaller than the NOBLs described in this study (FIG. 6A). NOBLs have a bimodal volume-weighted size distribution with a primary peak at 2.5 μm and variable, secondary peak at 11 μm. This size distribution has implications for clinical translation: nanosized NOBLs are small enough to pass through the pulmonary capillary bed yet large enough to permit strong cavitation nucleation from 1 MHz ultrasound exposure. However, these techniques present a trade-off between frequency-dependent ultrasound response and drug-loading capability, which are both highly dependent on particle size.

The size discrepancy between the primary peaks could be explained by the use of a novel NO/OFP blend in this study, compared with OFP alone used in the report by Endo-Takahashi et al. NO is more soluble in lipid than in aqueous solution, yet reacts more readily with oxygen in these environments. NO is further soluble in perfluorocarbon, demonstrated by prolonged release profiles in an in vivo hamster model. The results set forth here demonstrate that liposomes encapsulating both NO and OFP show more than an additive effect. The synergy appears most pronounced at approximately equal volume ratios, suggesting a 1:1 molal significance to the mechanism underpinning the observed synergy.

It was further observed that the presence of DOTAP, a cationic lipid, likely conferred an affinity to the anionic endothelial glycocalyx of the vascular walls, decreasing circulating time in vivo, which could necessitate local infusion and limit the applicability of NOBLs to tissues downstream from traditional intra-arterial access sites. Phospholipid emulsions with a minimum of cationic lipids, and without DOTAP are preferred. Enhanced targeting and localization near the endothelium may be achieved ultrasonically by use of acoustic pulses to optimize radiation force and acoustic streaming. The presence of long chain (PEG 2000) and short chain (PEG 500) polyethylene glycol has been used in certain embodiments of the liposomal formulations to mitigate potential immunogenicity and antigenicity, which results in a prolonged circulation time. In the present model, bubble liposomes were injected directly into the lumen of the arterial ring, where they were exposed to 30 cycle pulses of 1 MHz ultrasound at a peak-to-peak acoustic pressure amplitude of 0.34 MPa. Hemoglobin at in vivo concentrations would completely quench NO produced within the lumen of a blood vessel, thus necessitating NO delivery in close proximity to the endothelium.

Ultrasound Exposure and Cavitation Utilizing Pulsed Ultrasound.

The data presented here demonstrate that strong relaxation by NO-loaded liposomes can be enhanced by ultrasound exposure at acoustic pressures lower than previously described. In this study, vascular relaxation was triggered from NOBLs with pulsed ultrasound at a peak-to-peak acoustic pressure amplitude of 0.34 MPa. Despite the detection of strong cavitation at this acoustic pressure, the precise mechanism of NO release and delivery remains unclear. At a 0.34 MPa pressure exposure, it is likely that NO was released from the bubble liposomes gradually over a number of acoustic cycles. Other investigators have detected loss of echogenicity from contrast agents at acoustic pressures below the stable and inertial cavitation thresholds. In prior experiments using Definity® and echogenic liposomes, the onset of stable and inertial cavitation was concomitant with an 80% loss of echogenicity.

Figure 5:
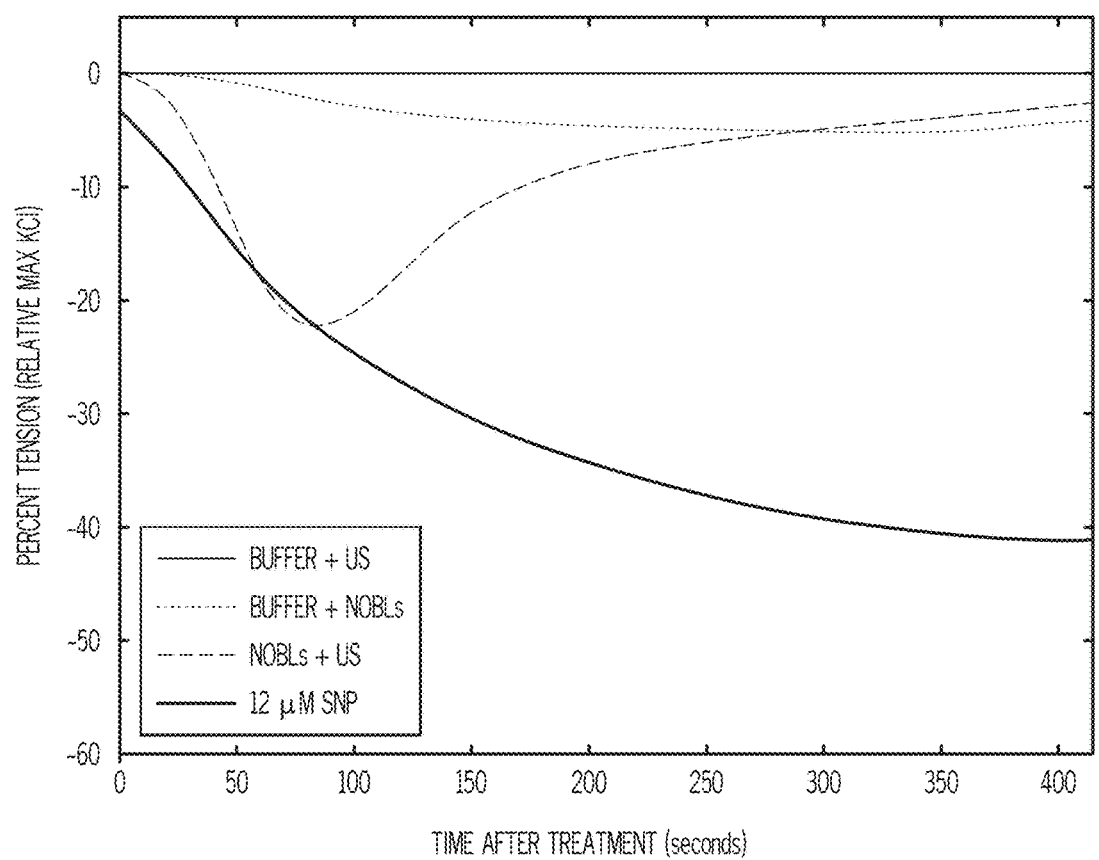
FIG. 5. Graph illustrating representative tension reduction (relative to the maximum KCl contraction tension) for buffer+US, buffer+NOBLs, NOBLs+US (peak-to-peak acoustic pressure amplitude 0.34 MPa), and control agonist sodium nitroprusside. Each treatment's minimum tension (maximal relaxation) was used for grouped analysis. (Abbreviations: SNP, sodium nitroprusside; NOBLs, nitric-oxide loaded bubble liposomes; US, ultrasound, KCl, potassium chloride)

In this study, OFP appeared to stabilize NO within the bubble liposomes prior to activation by ultrasound and the combination provided a synergistic benefit. Without intending to be bound by theory, the different properties of these gases (eg, molecular size, solubility) could promote a differential diffusion profile during acoustically driven oscillation. Upon membrane distention during volumetric bubble expansion, NO would likely dissolve more readily in the surrounding aqueous medium due to its high solubility. Also, after liberation of NO, the residual OFP bubble activity could promote microstreaming and enhanced convection and penetration into nearby vascular tissue. The diffusivity of NO, roughly 3,300 $\mu m^2$ per second in muscular tissue, is high enough to support a linear diffusion distance of roughly 250 µm (approximate radial depth of porcine carotid smooth muscle cells) over several seconds. NOBL infusions with ultrasound exposure consistently caused sharp decreases in vascular tension, typically occurring in the order of tens of seconds, followed by a steady tension restoration period, which lasted several minutes (FIG. 5).

Vasorelaxation

Arterial segments relaxed significantly more when treated with NOBL infusions in the presence of pulsed ultrasound, compared with infusions with NOBLs alone (FIG. 8). The ability of ultrasound to promote the delivery of encapsulated NO to vascular tissue agrees with observations by previous investigators. Using NO-loaded echogenic liposomes, increased vasodilation of rabbit carotids after exposure to 5.7 MHz color Doppler ultrasound at a peak negative acoustic pressure of 0.35 MPa has been demonstrated. Huang et al used a mixture of NO and argon gas to encapsulate or "cage" the NO and trigger effective release to porcine carotid tissue. In this study, the release of NO from the liposome into the surrounding medium was decreased by roughly 65% using the argon/NO mixture. At lower peak-to-peak pressure amplitudes (<0.40 MPa), other encapsulated bioactive gases, such as xenon, have been shown to exhibit enhanced release and delivery profiles with ultrasound. Other studies have demonstrated the feasibility of encapsulating NO or NO-yielding molecules to prevent physiologic degradation. For example, McKinlay et al demonstrated strong vasorelaxation of porcine coronary rings incubated with NO bound within a porous organic metal framework.

System Development

Although the ultrasound tissue bath system is capable of providing real-time feedback on NO delivery to vascular tissue, it has a few limitations. Here, a volatile anesthetic was used to sedate the animals prior to carotid excision, which can reduce endothelium function significantly by inhibiting endothelial production of NO. Cavitation near the vascular endothelium during UMDD is hypothesized to liberate endothelial NO synthase from membrane-bound proteins, such as caveolin-1. Increased cytosolic endothelial NO synthase results in increased endothelium-derived NO, an effect likely absent in the present model.

During arterial precontraction, porcine hemoglobin was diluted into the reservoir to a concentration of 1 g/L. At this concentration, arteries consistently re-established equilibrium contraction tension following NO-induced vasorelaxation. This was likely due to the quenching of excess NO by hemoglobin, a reaction well documented in vivo. Because free hemoglobin quenches NO a thousand times faster than hemoglobin within intact erythrocytes, the presence of free hemoglobin in the bath likely resulted in a weaker vasorelaxation than expected in vivo in the absence of hemolysis.

The system described here also implemented an infusion of treatment combinations directly to the lumen of the vessel. This approach, while likely difficult to replicate in vivo, ensured steady replenishment of drugs and bubbles during experimental treatment, and permitted simple adaptation of a previously established tissue perfusion model. An infusion of 12 µM sodium nitroprusside, directly infused into the lumen of the artery, likely only remained in the arterial lumen for a few seconds before being dispersed throughout the large reservoir filled with Krebs buffer. Together, these changes may have resulted in a much lower amount of sodium nitroprusside, and its product NO, delivered to the vascular rings compared with preparations using sodium nitroprusside in traditional tissue bath systems.

Smooth Muscle Relaxation

In vivo, NO-mediated modulation of smooth muscle tone is well described by two biochemical pathways: (a) stimulation of guanosine 3':5' cyclic monophosphate (cGMP) and adenosine 3':5' cyclic monophosphate and (b) direct modulation of calcium-activated, potassium channel (K+Ca) permeability. Bolotina et al. ("Nitric oxide directly activates calcium-dependent potassium channels in vascular smooth muscle" Nature. 1994; 368(6474):850-853, the entire disclosure of which is incorporated herein by this reference), describe the effect of exogenous NO on cGMP and K+Ca. These authors observed that cGMP-mediated vasorelaxations from exposure to NO were transient in nature and concentration-dependent, as determined by quantifying maximal relaxation, which is the metric used here. Due to the potential for sensitivity to the K+Ca-dependent pathway of NO-mediated vasorelaxation, integrated relaxation could be considered as a potential metric in future applications of this system, and may assist in understanding the temporal nature of ultrasound-mediated NO release from bubble liposomes.

The ultrasound tissue bath system described here demonstrates a novel, effective technique to characterize ultrasound-mediated delivery of a bioactive gas to vascular tissue. Ultrasound tissue bath systems can be used to monitor UMDD in real time. The data presented demonstrate that NO can be released from bubble liposomes with 1 MHz pulsed ultrasound exposure and deposited into vascular tissue. Pulsing provides a greater benefit than continuous US exposure. NO penetration into tissue causes potent vasorelaxation, which manifests as a change in isometric vascular tension. Although both NO-loaded liposome and CFP-loaded liposome are known, an unexpected synergistic effect occurred when liposomes were loaded with both NO and CFP. There is an increasing synergy observed until the volume of CFP approximately equals the volume of NO, indicating a mechanism that relies on a 1:1 molecular effect. The benefits of pegylation appear unexpectedly related to the type of gas encapsulated in the liposome, and the composition of the bubble lipid shell.

Example 2

This Example characterizes and compares ELIP loaded with different gas compositions.

Gas diffusion is a key process that directly impacts the stability of an agent. Without an encapsulating shell, an air bubble with initial diameter of 2 μm in water at 37° C. is predicted to fully dissolve within 25 ms. Thus, the phospholipid shell plays a critical role in the stability of echogenic liposome formulations. The gas permeability of the shell material has the largest effect on the stability of a ultrasound contrast agent. However, the material permeability is difficult to model for phospholipid-shelled UCAs such as ELIP. Thermodynamic factors may affect the molecular packing of the surface active molecules that make up the shell and influence the effective material properties. A strategy employed in second generation UCAs such as Definity® was to replace air with a less soluble gas in order to extend dissolution time in vivo.

In order to develop new types of UCAs suitable for both diagnostic and therapeutic use, the stability of candidate agents in vitro were quantified and compared to gauge their longevity in solution. A series of novel formulations of echogenic liposomes with different shell components and gas content were characterized acoustically and compared. The shell components were modified by incorporating a polymer material for stabilizing the agent. The gas content of the agents investigated included a biologically inert high molecular weight gas, octafluoropropane ($C_3F_8$), and two physiologically active gases: Nitric oxide (NO) and Xenon (Xe). Individually, UCAs comprising these gases are known. Nitric oxide has potent vasoactive effects and may be used to improve treatment of both atherosclerosis and ischemic stroke. Xenon (Xe) is an NMDA-receptor antagonist which functions as a neuroprotectant. Locally administered xenon gas has been shown to limit neuronal damage from oxygen deprivation caused by ischemia-reperfusion injury (Ma et al. 2002; Britton et al. 2010; Peng et al. 2013). As noted above, OFP has been incorporated in phospholipid-shelled UCAs where a bioactive gas is not the UCA payload, as a replacement for air due to its slower dissolution time in vivo. Through measurement of the broadband attenuation over time, the dissolution profile of these newly developed formulations of echogenic liposomes are characterized.

Echogenic Liposome Preparation

Echogenic Liposomes (ELIP)

Two different ELIP preparations were used. Both preparations began with a formulation parameter known in the art and first described by Buchanan et al. (2008), in which approximately two-thirds of the unsaturated phosphatidylcholine (EggPC) was replaced with saturated dipalmitoyl-phosphatidylcholine.

The first "enhanced ELIP" formulation comprises 1,2-dipalmitoyl-sn-glycero-3-phosphocholine (DPPC), L-α-phosphatidylcholine (EggPC), 1,2-dipalmitoyl-sn-glycero-3-phosphoethanolamine (DPPE), 1,2-dipalmitoyl-sn-glycero-3-phospho-(1'-rac-glycerol) (DPPG) and cholesterol (CH) in a molar ratio of 27:42:8:8:15. Stability of this formulation is demonstrated at physiologic temperature. It was further demonstrated that this formulation yielded higher ultrasound attenuation than the 69:8:8:15 formulation first described by Huang et al. (2002).

The second formulation, referred to herein as "pegylated ELIP," was modified by incorporating a synthetic polymer compound to achieve a longer circulation time in vivo. Poly-(ethylene glycol) (PEG) is a hydrophilic compound with a flexible oligomer chain that can be incorporated on the liposome surface to act as a steric stabilizer and delay circulatory clearance by phagocytosis. PEG groups are referred to by numbers that indicate the average molecular weight, and are normally anchored to the lipid surface via a cross-linked lipid such as DPPE. In pegylated ELIP, DPPE is replaced with DPPE-PEG2000. The pegylated ELIP formulation comprises DPPC, EggPC, 1,2-dipalmitoyl-sn-glycero-3-phosphoethanolamine-N-[methoxy(polyethylene glycol)-2000] (DPPE-PEG2000), DPPG, and CH in a molar ratio of 28:43:6:8:15.

All ELIP were prepared using the freeze-lyophilization method described by (Huang 2010) and reconstituted from lyophilized powder. Lipids were purchased from Avanti Polar Lipids (Alabaster, Ala., USA). ELIP formulations were stored at 4° C. in lyophilized powder form in 2-mL clear glass vials (C4013-1, National Scientific; Rockwood, Tenn., USA) with PTFE and silicone septa (C4013-60, National Scientific) until use.

Prior to reconstitution, vials containing lyophilized ELIP powder were evacuated (−635 torr) and subsequently re-pressurized by adding 4 mL of gas mixture (2 atm) to the sealed vial using a syringe. The vials were "re-charged" in this way to insure that the desired gas mixture was not affected by shipment or storage. The gas mixture consisted of one of OFP gas (Specialty Gases of America, Toledo, Ohio, USA), a mixture of NO (10%) gas (Sigma-Aldrich, St Louis, Mo., USA) and OFP (90%) gas, or a mixture of xenon (Xe, 90%) gas (Concorde Specialty Gases, Eatontown, N.J., USA) and OFP (10%). The vials remained pressurized for at least 45 minutes before use. Summarily the liposomes comprised OFP alone, 1:9 NO+OFP, and 9:1 Xe+OFP. As detailed in Example 1, data was also generated by the same investigators for an approximately 1:1 NO+OFP gas mixture. Liposomes comprising NO or OFP or Xe alone are known and have been characterized in the art.

Stock suspensions of gas-loaded ELIP were prepared by venting the excess gas pressure by inserting a 22-gauge needle through the septum and immediately injecting 0.5 mL air saturated, filtered (0.2-μm) and deionized water (NANOPure, Barnstead International, Dubuque, Iowa, USA) water at room temperature (20-24° C.) through the septum using a separate 22-gauge needle, yielding a stock solution with a lipid concentration of 10 mg/ml. All ELIP were used immediately following reconstitution.

Bubble Liposomes (BLs)

The BLs containing either OFP gas or a mixture of NO and OFP were prepared using methods similar to those described by Endo-Takahashi et al. (2012) for cationic bubble liposomes. The liposomal formulation comprised DPPC, 1,2-dioleoyl-3-trimethylammonium-propane (DOTAP), 1,2-distearoyl-sn-glycero-3-phosphoethanolamine-N-[methoxy(polyethylene glycol)-2000] (DSPE-PEG2000), and 1,2-distearoyl-sn-glycero-3-phosphoethanolamine-N-[methoxy(polyethylene glycol)-750] (DSPE-PEG750) in a 79:15:3:3 molar ratio. Lipids were dissolved in 9:1 chloroform/methanol in a 500-mL round-bottom flask and the organic solvent was completely removed by evaporating at 47° C. using a rotary evaporator (N-1001, Eyela USA, Bohemia, N.Y., USA). Phosphate-buffered saline (1 mL/mg lipid) was added to re-hydrate the lipid solution and the mixture was sonicated for 5 min to form bubble liposomes. After sonication, 1 mL aliquots of the liposomal emulsion were pipetted into 2-mL glass vials (National Scientific C4013-1; Rockwood, Tenn., USA) and capped with PTFE and silicone septa (National Scientific C4013-60). The vials were evacuated using a laboratory wall vacuum (−635 torr) and stored at 4° C. until use. Immediately prior to use, the vials were allowed to warm to room temperature (20-24° C.) and 2.5 mL of gas mixture was injected into the vial headspace through the septum using a 22-gauge needle. The gas mixture consisted of OFP or a 90:10% mixture of OFP and NO gas (Sigma-Aldrich, St Louis, Mo., USA). The vial was mechanically agitated by shaking vigorously for 45 seconds (Vialmix®, Bristol-Myers Squibb Medical Imaging, North Billerica, Mass., USA) and allowed to equilibrate to room temperature. Immediately prior to experimental use, the cap was removed and BLs were pipetted into the reservoir.

Definity®

The stability of ELIP, pegylated ELIP, and bubble liposomes containing various gas mixtures was measured and compared with Definity® (Lantheus Medical Imaging, North Billerica, Mass., USA), an FDA approved ultrasound contrast agent consisting of OFP gas encapsulated by a lipid shell. Vials of Definity® were activated according to the manufacturer's instructions. A summary of the agents and dilution ratios used in this study for broadband attenuation measurements versus time is given in Table 1.

TABLE 1

| Agent: | Gas | Dilution Ratio |
|---|---|---|
| Definity | $C_3F_8$ | 1:2000 |
| ELIP | Air | 1:200 |
|  | $C_3F_8$ | 1:200 |
| Pegylated ELIP | Air | 1:100 |
|  | $C_3F_8$ | 1:100 |
|  | $NO:C_3F_8$ | 1:200 |
|  | $Xe:C_3F_8$ | 1:200 |
| Bubble lipsomes | $C_3F_8$ | 1:200 |
|  | $NO:C_3F_8$ | 1:200 |

Particle Size Measurement

The initial size distribution and number density of each agent was measured using a Coulter counter (Multisizer 4, Beckman Coulter, Brea, Calif., USA). The number density of particles (corrected for dilution) was plotted as a histogram consisting of 200 bins on a logarithmic scale from 0.6 to 18 μm. The volume weighted size distribution was calculated from the number of particles per unit volume within each bin. The mean and standard deviation of the total number density and total particle volume was computed from the distributions.

Attenuation Versus Time Measurement

For each sample, the frequency-dependent attenuation was measured as a function of time. The frequency-dependent attenuation was measured at 37° C. in PBS with 0.5% bovine serum albumin solution using the broadband substitution technique. The only modification to the system was the introduction of a magnetically coupled stir bar to permit continuous mixing of the agent in the sample chamber while performing measurements of the acoustic attenuation over time.

Mixing

Figure 10:
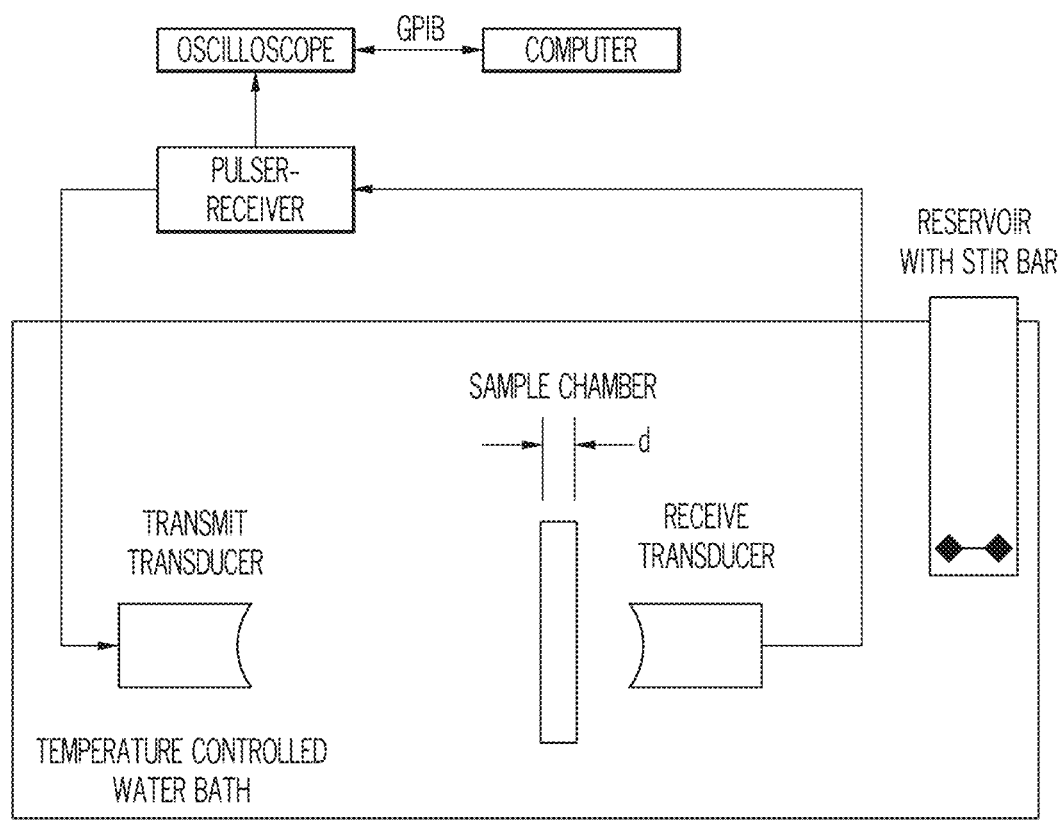
FIG. 10. A schematic representation of the attenuation measurement setup is depicted. A pair of broadband PVDF transducers are employed to acquire the spectrum using a substitution technique. A pulser-receiver was used in through-transmission mode to generate the excitation pulse and amplify the received signal. Samples of UCAs in diluent or diluent alone were added to the reservoir and introduced into the sample chamber by gravity feed.

During measurement, the suspension was mixed continuously to prevent aggregation of bubbles and to insure homogeneous distribution for each acquisition. The mixing was performed using a 1.5 mm×8 mm teflon coated magnetic stir bar placed inside the sample chamber (FIG. 10) through one of the Luer-lock ports. A neodymium rare earth disc magnet (0.38" OD×0.25" ID×0.06" thick; R621 K&J Magnetics, Pipersville, Pa., USA) was mounted vertically on the end of a 0.5" steel optical rod shaft and rotated using a DC motor (9-18V model #273-256; Radio Shack, Fort Worth, Tex., USA). The force from the disc magnet kept the stir bar suspended and rotating smoothly (~200-600 rpm) in the sample chamber at a location immediately adjacent to the acoustic field. Stirring in this manner did not have any perceivable effect on the acoustic attenuation measurement of diluent alone. Stirring was turned on immediately after the first acquisition and remained on for the duration of the measurements. The attenuation spectrum was measured at least once every 60 s over a period of 90 min.

Data Reduction and Analysis

Data reduction was accomplished by developing metrics to describe the frequency range over which each agent was most attenuative, as well as an estimate of the length of time that the agent was stable. The frequency range is described by the interval over which the initial attenuation spectrum is within ~3 dB of its maximum value, given as $\Delta f_{-3\ dB}$ (see Table 2). The time evolution is described by tracking the value of the mean attenuation in the initial $\Delta f_{-3\ dB}$ frequency interval at each of the measured time points. The time at which this value falls by 3 dB from its maximum ($t_{-3\ dB}$) is used as a metric to describe the dissolution of the gas. Similarly, the time at which the maximum attenuation is measured is given as $t_{max}$.

Results

Acoustic attenuation measurements were made to assess temporal stability of ELIP containing OFP gas. The mean number density and volume-weighted size distribution were plotted versus particle diameter. The measured attenuation coefficients as a function of frequency were calculated at 0, 30, 60, and 90 min.

TABLE 2

| Agent | Gas | Diameter Mode (μm) | Number Density (#/mL) | $\Delta f_{-3\ dB}$ (μm³/mL) | $t_{max}$ | $t_{-3\ dB}$ |
|---|---|---|---|---|---|---|
| Definity | $C_3F_8$ | 2.4 | 5.2 ± 0.8 | 4.6-8.8 | 0 | 18 |
| ELIP | Air | 1.7 | 30 ± 4 | 6.8-15.0 | 8 | 45 |
|  | $C_3F_8$ | 0.8 | 325 ± 12 | 18.0-25 | 5 | 23 |
| Pegylated ELIP | Air | 0.7 (18) | 27 ± 2 | 2-2.4 | 4 | 10 |
|  | $C_3F_8$ | 3.0 | 135 ± 49 | 2-3.8 | 0 | 15 |
|  |  |  |  | 11.0-25 | 1 | 56 |
|  | $NO:C_3F_8$ | 1.3 | 184 ± 54 | 7.6-22.0 | 12 | 16 |
|  | $Xe:C_3F_8$ | 2.7 | 58 ± 15 | 4.6-25 | 6 | 82 |
| Bubble lipsomes | $C_3F_8$ | 0.8 | 32 ± 2 | 22.8-25 | 4 | 62 |
|  | $NO:C_3F_8$ | 2.0 | 27 ± 7 | 21.8-25 | 9 | 78 |

The frequency-dependent attenuation over time for several formulations of echogenic liposomes with different shell components and gas content listed in Table 1 were measured (data not shown). Comparative data for a series of agents, producing characteristic attenuation curves as well as derived metrics that describe the evolution of the attenuation over time (dissolution profile) were generated and are set forth in Table 2. A clear influence of the formulation on the size distribution and the measured attenuation curves was observed. For example, Definity® was found to exhibit a bimodal volumetric size distribution, in agreement with earlier studies. Using the shell elasticity parameter previously determined for Definity® at 37° C. ($S_p$=1.1 N/m), it was found that the initial peak attenuation frequency range ($\Delta f_{-3\ dB}$) corresponds to bubbles with a mean diameter of 1.9-3.0 µm. Bubbles larger than ~4 µm in the bimodal distribution influence the attenuation frequency spectrum primarily at frequencies <3 MHz, as has been shown in previous studies. Similarly, using the shell elasticity parameter previously determined for enhanced ELIP at 37° C. ($S_p$=3.1 N/m), it was found that the initial peak attenuation frequency range ($\Delta f_{-3\ dB}$) corresponds to bubbles with a mean diameter of 1.8-3.1 µm. The attenuation for air-loaded ELIP initially increased, reaching the largest value at 8 min. Moreover, the attenuation at low frequencies (<10 MHz) decreased and the frequency of peak attenuation shifted to a slightly higher value. This suggests that gas may be diffusing out of larger ELIP initially, with the majority of microbubbles stabilizing at a mean diameter of ~2 µm, which is the resonance size corresponding to 12.5 MHz. The majority of phospholipid-shelled microbubbles undergoing dissolution tended to stabilize in a fairly narrow size range (1-2 µm) independent of initial microbubble size or phospholipid composition.

Stability of Pegylated ELIP

The influence on the stability of ELIP agents by incorporating PEG into the ELIP encapsulation or replacing air with a less soluble gas was studied. Pegylation (i.e., the covalent attachment of PEG) is known to enhance the aqueous solubility of hydrophobic drugs, prolong circulation time, minimize nonspecific uptake, and increase nanoscale therapeutic drug accumulation through the enhanced permeability and retention effect. The incorporation of PEG has a steric stabilizing effect and has been an important step in the development of long-circulating liposomes.

By comparing the results acquired for ELIP with and without pegylation, an enhancement of stability when PEG is added into the formulation for agents that contain OFP gas, but not air was observed. ELIP containing air were much more stable (45 min) than pegylated ELIP loaded with air (10 min). This suggests that pegylation is not suitable for air-loaded ELIP, possibly because the large polymer chain molecules make the shell more permeable (or less stable) and the air rapidly dissolves into solution. However, the opposite appears true for OFP-loaded agents, which tend to stabilize at smaller sizes and produce attenuation spectra dominated by high frequencies (>10 MHz) compared with air-loaded agents. Pegylated ELIP containing OFP gas last much longer (56 min) than ELIP containing OFP gas (23 min). The longevity might be due to a steric stabilization effect of PEG that reduces the surface tension and effectively counteracts the Laplace pressure for even smaller particles so that they are able to last longer.

Pegylated ELIP containing air had the largest modal diameter of ~18 µm, although the size distribution peak was not able to be fully characterized due to the limitation of the maximum size that could be measured with the 30 µm aperture tube on the Coulter counter. This distribution was characterized by a distinct attenuation curve that is more or less flat at high frequency (geometric scattering) and increases rapidly at low frequencies.

Pegylated ELIP containing a mixture of NO and OFP contained a relatively higher proportion of smaller particles (<2 µm) within the population, and exhibited a correspondingly higher and much broader frequency range (7.6-22.0 MHz). The attenuation increased over 12 min. After an initial growth phase, the attenuation began to decrease and the peak shifted to lower frequencies, possibly indicating bubble expansion (growth) or coalescence. Once this phenomenon occurred, the −3 dB decay time was 16 min, possibly indicating large unstable bubbles or flotation out of solution. Pegylated ELIP containing a mixture of Xe and OFP yielded a relatively flat attenuation curve above 10 MHz.

Stability of Agents Containing OFP Gas

The stability of Definity® was compared to ELIP and bubble liposomes that also contain OFP gas. Each of the other three agents, ELIP, pegylated ELIP and bubble liposomes, retained attenuation in the high frequency range longer than Definity®. This longevity may be due to a relatively higher proportion of smaller, stabilized bubbles that persist in solution over a longer period of time. Pegylated ELIP also exhibited a distinct low frequency peak (~2-2.4 MHz) in the attenuation spectrum which decayed in about the same time (15 min) as Definity® (18 min). This temporal pattern may be due to a small fraction of large bubbles in the >4 µm range, which correspond to the population of Definity® particles the in the same size range.

Stability of Agents Containing NO Gas

The measured attenuation for agents containing NO gas increased initially after dilution 12 min for pegylated ELIP and 9 min for bubble liposomes, indicating that NO has a strong and prolonged osmotic effect. A shift in the attenuation peak to lower frequencies over time was evident for this formulation, which may indicate bubble expansion (growth) or coalescence of smaller bubbles over time leading to larger bubbles which have a lower resonance frequency. In comparison, the attenuation of agents containing OFP gas alone (including Definity®) increased only for the first 5 min. For OFP-loaded agents, the initial growth phase may happen very rapidly and may occur before the first measurement.

Stability of Bubble Liposomes

The preparation method appeared to have a strong impact on the characteristic attenuation profile over time. Bubble liposomes, which were prepared by vigorous shaking using a VialMix®, showed a broader size distribution and attenuation spectrum than ELIP, which are reconstituted from lyophilized powder. The attenuation coefficient of bubble liposomes is distinct and increases with the frequency up to the limit of the measured frequency range (25 MHz).

The stability of a particular agent is shown to be influenced by multiple factors. Besides the shell composition and the gas content, the agent concentration and the size distribution of the sample can also play a role. For example, the sample concentration of pegylated ELIP containing a mixture of NO and OFP ($184 \times 10^6$ per mL) is more than three times higher than PEGylated ELIP containing a mixture of Xe and OFP ($58 \times 10^6$ per mL). Compared to the approaches used in other bubble characterization studies, in which individual particles are characterized, the attenuation spectroscopy method used here can provide information about the behavior of a population of agents.

Clinical Implications

The results suggest distinct features of the different formulations of ELIP which have relevance for clinical applications. Pegylated ELIP containing xenon showed a lower attenuation but a prominently higher stability than nitric oxide-loaded ELIP. This data suggests a much longer circulation time and relatively stable performance of the former group in vivo. On the other hand, NO-loaded ELIP may be suitable for acute clinical treatment over shorter time durations, since this agent remains stable and increases attenuation during the initial 12 min after dilution. The effect of passive gas diffusion must be considered due to the strong osmotic effect. However, this behavior is expected to be less significant for NO-loaded bubble liposomes than for NO-loaded pegylated ELIP. Such passive diffusion has not proven to be a problem in previous in vitro bioactive gas release experiments with NO-loaded bubble liposomes. The reconstitution methodology can be tailored for individual clinical applications. Bubble liposomes were more attenuative in the high frequency range (>15 MHz). Therefore, bubble liposomes may be more suitable for high-frequency ultrasound imaging or photoacoustic imaging.

Example 3

This example illustrates release of gas from ELIP exposed to ultrasound.

Introduction

Micron-sized encapsulated bubbles are widely used as a blood pool ultrasound contrast agent (UCA) for diagnostic imaging. The gas core provides a large impedance mismatch with tissue which is highly reflective to ultrasound. Microbubbles can also be readily destroyed during ultrasound imaging using pulses with peak rarefactional pressures larger than about 1 MPa. Following a destruction pulse, the assessment of perfusion of new contrast agent microbubbles flowing into a depleted region can assist diagnosis of cardiac ischemia and angiogenic tumors. Disruption-reperfusion imaging, together with flash echo (Kamiyama et al. 1999) and stimulated acoustic emission imaging (Blomley et al. 1999), are novel imaging methods utilizing the intentional destruction of UCA microbubbles. Ultrasound-mediated UCA destruction (Schroeder et al. 2009) has also been proposed as an essential part in certain therapeutic applications, such as localized drug delivery (Unger et al. 2004; Sutton et al. 2013) and thrombolysis (De Saint Victor et al. 2014).

The relationship between cavitation and ultrasound-induced UCA destruction has been the subject of previous investigations. Both acoustical measurements and high-speed optical observations have measured an acoustic pressure threshold above which irreversible destruction of UCA ensues. The destruction threshold varies with the frequency, pulse length and the strength of the encapsulating shell. Two regimes have been identified based on the temporal characteristic of UCA disruption. At relatively low pressures (MI<0.2), vibrations of microbubbles driven by sufficient acoustic pressure can disrupt the shell and result in acoustical driven diffusion of the gas, resulting in deflation or shrinkage of the microbubble. At a higher pressure regime (MI>0.2), the bubble expansion ratio can become so large that the wall acceleration is dominated by the inertia of the surrounding fluid, leading to violent collapse of the bubble. During this process the bubble can fragment or break into small pieces and emit broadband noise (Neppiras 1980).

Special attention has been given to the evolution of UCA response when exposed to pulsed ultrasound. Exploration of the behavior of acoustically driven UCAs has helped to develop contrast specific imaging methods and drug delivery procedures. Experiments using a pulse-echo technique suggested an enhancement in backscattering immediately after UCA disruption. This phenomenon was explained by the decrease in shell damping or by a passage of the bubble through the resonant size during dissolution. Ultra-high-speed imaging studies of single bubbles exposed to multiple pulses of ultrasound revealed microbubble deflation over each pulse. The response amplitude was also observed to increase for microbubbles close to resonance size.

Investigations of UCA response have been further extended to echogenic liposomes (ELIP), which are recently developed agents showing potential for theragnostic utility. ELIP are phospholipid vesicles that encapsulate both gas microbubbles as well as aqueous cores. Pressure thresholds for both acoustically driven diffusion and rapid fragmentation of ELIP have been identified by using pulsed Doppler sequences from a clinical diagnostic scanner. In later studies, the loss of echogenicity from ELIP exposed to pulsed Doppler ultrasound was correlated with acoustic emissions in an attempt to understand the destruction process. Rupture of the shell is thought to play a role in liberation of gas from ELIP. However, the mechanism responsible for loss of echogenicity at pressure levels below the stable or inertial cavitation threshold is unknown.

This example involves investigation of the response of ELIP microbubbles stabilized by a lipid shell to pulsed ultrasound with a 6-MHz center frequency. An ultra-high-speed imaging camera operating at $19 \times 10^6$ frames per second was used to measure the radius versus time dynamics of ELIP in response to 5 consecutive tone bursts over a duration of 400 ms. An optical approach was used to study the destruction phenomena for ELIP (e.g. dissolution, fragmentation) in detail. In some cases, a rapid size reduction was observed during the ultrasound excitation. The dependence of the size reduction on the dilatation rate was explored. Surface mode vibrations, which are hypothesized to be related to bubble fragmentation, were also observed and shown to depend on the pressure and initial bubble radius.

Experimental Setup

Freeze-dried ELIP dispersions consisting of EggPC/DPPC/DPPE/DPPG/Cholesterol (27:42:8:8:15, mol %) were prepared as previously described. ELIP were prepared at the University of Texas Health Science Center (Houston, Tex., USA) and shipped overnight to Erasmus Medical Center (Rotterdam, the Netherlands) with refrigerant packs (4° C.) in lyophilized powder form. The lyophilized lipid powder was reconstituted using air saturated, filtered (Type I) water at room temperature, resulting in stock suspensions of ELIP at a lipid concentration of 10 mg/mL. The stock suspension was diluted (~100×) in air saturated phosphate-buffered saline (PBS) mixed with 0.5% (w/v) bovine serum albumin (BSA) solution (Sigma Chemical Co., St. Louis, USA). The diluted suspension was injected into an Opti-Cell® (Nunc/Thermo Scientific, Wiesbaden, Germany) and placed on a microscope optical stage in a 37° C. water bath for imaging using a microscope (Olympus, Zoeterwoude, the Netherlands) with a 60× water-immersion objective. The total magnification of the system was increased to 120× using a 2× magnification lens inside the microscope. A xenon flash lamp (A-260, Vision Light Tech, Uden, the Netherlands) with a fiber-optic light guide (SCHOTT AG, Mainz, Germany) was used to illuminate the optical region of interest for the ultra-high-speed recordings. A diagram of the ultra-high-speed optical imaging setup is presented in FIG. 10. Recordings of the bubble dynamics consisting of 128 frames were captured at approximately 19×10⁶ frames per second using the ultra-high-speed framing camera Brandaris 128.

Acoustic Excitation Pulse

The excitation waveforms and acoustic pressure amplitude range chosen for this investigation were selected based on the results of previous investigations on ELIP by Smith et al. (2007) and Radhakrishnan et al. (2013). In the previous studies, 6-MHz duplex spectral Doppler waveforms from a standard clinical diagnostic scanner equipped with a peripheral vascular probe (HDI 5000 with L12-5 linear array transducer, Philips Medical Systems, Bothell, Wash., USA) were used to investigate loss of echogenicity from ELIP and cavitation thresholds. Radhakrishnan et al. (2013) observed ~80% loss of echogenicity at acoustic pressure amplitudes well below the measured stable or inertial cavitation thresholds, which were found to be ~500 kPa and ~630 kPa, respectively. To investigate the behavior of individual ELIP excited acoustically, four acoustic pressure amplitudes were selected which were sufficient to result in observable bubble motion in the optical recording but below the inertial cavitation threshold determined previously.

Acoustic excitation tone bursts similar to the Doppler waveforms used in previous studies consisted of a 20-cycle sinusoidal wave with a cosine envelope and a fundamental frequency of 6 MHz. Waveforms were generated using a programmable arbitrary waveform generator (8026, Tabor Electronics Ltd., Tel Hanan, Israel) and amplified using a wideband RF amplifier (0.3-35 MHz, A-500; Electronic Navigation Industries, Rochester, N.Y., USA) before being routed to a focused, broadband PVDF transducer (PA275; Precision Acoustics, Dorchester, United Kingdom). The transducer had a diameter of 23 mm, and focal distance of 25 mm, with a −6 dB frequency bandwidth from 2.0-13.5 MHz. The transducer was positioned in the water bath at a 45° angle below the sample and the acoustic focus (0.5 mm full-width at half-maximum pressure) was aligned with the optical region of interest.

The acoustic pressure at the four driving amplitudes used in this study was calibrated using a 0.2-μm PVDF needle-type hydrophone (Precision Acoustics Ltd., Dorchester, UK). The hydrophone was positioned approximately 2 mm from the membrane of a modified OptiCell® with one of the membranes removed and the peak acoustic pressure in situ at the location of the bubble during the optical recordings was determined to be 110, 250, 410, or 580 kPa. The transmitted acoustic pressure was attenuated by a factor of about 3 dB relative to the free-field pressure due to the presence of the OptiCell® membrane and the 45° angle of incidence of the acoustic wave.

Data Reduction and Analysis

The Brandaris 128 ultra-high-speed camera is able to store up to 6 sequences of 128 frames in memory, allowing multiple recordings in a single run. The timing between recordings is determined by readout of the CCD image sensors, which results in an approximate 80 ms delay between consecutive recordings (Chin et al. 2003). For each bubble selected for investigation, 6 recordings were acquired sequentially and transferred to memory. The first recording was acquired without ultrasound excitation to estimate the initial resting radius. For each of the subsequent recordings, an ultrasound tone burst at one of the driving pressure amplitudes (110, 250, 410, or 580 kPa) as described previously were applied. Using this scheme, each individual ELIP was acoustically excited 5 times at the same acoustic pressure over an interval of 400 ms. The bubble radius as a function of time, R(t), was measured from each recording using custom image analysis and tracking software developed in MATLAB (the Mathworks, Natick, Mass., USA) (van der Meer et al. 2007). Time-domain interpolation using the fast Fourier transform was used to recover the signal for analysis due to the low number of samples per cycle (~3) available from the optical recordings. The 128-point R(t) signal was resampled to 1024 equally spaced points using the MATLAB interpft routine. The original signal was transformed to the Fourier domain, zero-padded, and then transformed back with 8× more points.

Individual ELIP were exposed to 20-cycle acoustic bursts at one of the four pressure amplitudes described above. Each burst excitation was considered an independent trial. It was initially posited that surface mode oscillations manifest as oscillating asymmetric optical interference patterns with a frequency lower than the acoustic driving frequency. An impartial observer evaluated the recordings and indicated for each if a surface mode oscillation was observed (yes or no). The appearance of oscillating asymmetric optical interference patterns with a frequency lower than the pulsation mode frequency was taken to be indicative of a surface mode oscillation. Such oscillations did not preclude the recording from further analysis of the radius versus time response. The initial radius ($R_1$) and final radius ($R_2$) were estimated based on the mean value of the R(t) curve during the 8 frames at the beginning and end of the recording, respectively. In some cases, a noticeable change in radius ($\Delta R = R_2 - R_1$) as a result of the acoustic excitation was observed. The final radius was smaller than the initial radius, possibly due to acoustically driven diffusion of the ELIP vesicle occurring during the 20-cycle burst excitation. To simplify the analysis of the response amplitude when the instantaneous equilibrium radius is changing with time, the time derivative of the radius response which gives the microbubble wall velocity, $\dot{R}$, or dilatation rate, $\dot{R}/R$ were considered. The dilatation rate was calculated directly from the experimentally measured radius versus time curves.

Results

A total of 397 radius versus time curves for lipid encapsulated microbubbles with initial radii ($R_1$) ranging from 0.5-2.5 μm were analyzed. The results presented in this section are organized as follows. In the first two sections, phenomena observed in this study which stem from instabilities in the volumetric oscillations are described. In the second section, the radius versus time responses of ELIP undergoing stable volumetric oscillations are analyzed.

Fragmentation

Fragmentation of the microbubble into daughter bubbles was observed in 5 of 153 recordings at 410 kPa and 6 of 51 recordings at 580 kPa peak pressure. Fragmentation was not observed at 110 kPa or 250 kPa peak pressures. In a specific illustrative example, the initial radius, $R_1$, of the bubble is 0.75 μm (a frame before the ultrasound tone burst arrives). The microbubble begins compressing and expanding during the negative pressure half-cycle in subsequent frames. The compressed microbubble is not visible in the next frame. Upon rebound three fragments appear, which subsequently grow under the influence of the negative acoustic driving pressure. The fragments undergo several more oscillations before dissolving completely. For this example, the largest radius measured before fragmentation, $R_{max}$, was 1.5 μm giving an expansion ratio, $R_{max}/R_1 \sim 2$. The initial radius ($R_1$) and relative expansion ratio ($R_{max}/R_1$) for ELIP was observed and recorded. The initial radius was in a narrow range between 0.75-1.05 μm for all of the ELIP observed to fragment and the maximum expansion ratio was between 1.5 and 2.3.

Surface Modes

Asymmetric optical interference patterns indicative of surface mode oscillations were observed in 147 out of 397 total recordings. For example, a 2.2 μm liposome-encapsulated microbubble excited by 6-MHz tone burst with an peak pressure amplitude of 580 kPa. Asymmetric optical interference patterns are first visible in frame #32, after several cycles of acoustic excitation. During subsequent acoustic cycles, the surface mode oscillation amplitude grows and aspherical radial perturbations are evident about the perimeter of the microbubble. Observations of asymmetric interference patterns occurred primarily for bubbles larger than 1.5 μm, and a higher occurrence rate was found for larger pressures.

Stable Volume Oscillations

A total of 386 radius versus time curves for 88 individual ELIP exhibiting relatively stable volume vibrations were analyzed to monitor the evolution of radial response of ELIP under consecutive pulsed excitations. The data set includes recordings with stable volumetric oscillations both with (147) and without (239) surface modes. Within this regime, the volumetric expansion and compression can be derived by tracking radius versus time curves using the minimum cost algorithm. ELIP that fragmented or dissolved were not included in the analysis.

A total of 139 (36%) of the ELIP exposed to tone burst excitations exhibited a significant decrease in the resting radius before and after the acoustic excitation. A significant change is defined when the absolute size reduction of ELIP is greater than a predetermined resolution limit, $R_L$, characterized by $|\Delta R|=|R_2-R_1|\geq R_L$. For the experimental optical system used here, the stochastic error was established by determining the maximum radius variation for each quiescent microbubble during the first recording when no ultrasound was applied. The resolution limit, $R_L$, was taken as the mean value for all measurements which was 0.12 μm, or approximately 1.33 times the pixel size (90 nm$^2$) in the images (Emmer et al. 2007).

A typical radius versus time sequence consisting of 6 recordings for an individual ELIP undergoing acoustically driven diffusion is described. Deflation from an initial radius of 1.33±0.03 μm to 0.49±0.05 μm following 5 consecutive ultrasound bursts at 110 kPa peak pressure was observed. The deflation process takes place in stages. For each tone burst excitation, dissolution of up to 20% change in radius occurs during the microbubble response to the 3.33 μs acoustic excitation, and very little change in radius occurs during the relatively long acoustic quiescent time period (~80 ms) between recordings. Both the bubble size and the dilatation rate responses vary for each pulsed ultrasound exposure. The size reduction and dilatation rate are maximum for the second ultrasound tone burst (recording #3) as the liposome deflates and goes through an apparent resonance size (1 μm). The maximum dilatation rate was $2.3\times10^7$ s$^{-1}$ during the second ultrasound tone burst (recording #3) when the initial radius of the microbubble was 1.10±0.03 μm. The maximum dilatation rate decreases with each subsequent excitation with nearly complete dissolution (95% decrease in volume) after exposure to 5 tone bursts. An overlay plot of the absolute change in radius and maximum dilatation rate derived from each of the recordings, illustrates that these metrics are closely correlated.

Change in radius, $\Delta R$, as a function of the initial size due to single bursts at 110, 250, 410 and 580 kPa, respectively are recorded. A total of 139 (36%) of ELIP showed significant dissolution (defined as $\Delta R = R_2-R_1 < -R_L$) during a single burst excitation. The maximum change in radius was −21%, −29%, −46% and −43% for 110, 250, 410 and 580 kPa excitations, respectively. The maximum size reduction occurs for smaller bubbles. Those ELIP with an initial radius of 1 μm deflate the most in response to acoustic excitation for each of the maximum pressure amplitudes investigated.

Change in radius, $\Delta R$, as a function of the maximum dilatation rate are calculated from the radius versus time curves. Three regimes can be observed. At low dilatation rates ($<1\times10^6$ s$^{-1}$) a change in size either does not occur or is well below the resolution limit $R_L$. For moderate dilatation rates ($1\times10^6$ s$^{-1}$-$4.5\times10^6$ s$^{-1}$) the size variation is comparable to the resolution limit or uncertainty in the optical measurement ($R_L$). At higher dilatation rates ($>4.5\times10^6$ s$^{-1}$) all of the measured bubbles dissolve to a certain degree. The mean square error (MSE) estimator, a change point analysis approach based on segmented linear regression, was used to detect the change of size reduction as a function the dilatation rate (Luan et al. 2014). The change point at a dilatation rate of $4.5\times10^6$ s$^{-1}$ demarcates the threshold for the occurrence of ELIP dissolution.

Discussion

Rapid Fragmentation

Fragmentation of a phospholipid encapsulated bubble into smaller bubbles is a common phenomena that has been described in detail previously. One likely mechanism is that instabilities generated during the inertially driven collapse of a gas nucleus to a very small diameter become accentuated during the subsequent growth phase, causing the bubble to break up upon rebound. The inertially driven collapse also promotes broadband acoustic emissions, which have been used extensively to characterize the threshold for fragmentation of ELIP, as well as other UCAs. Breakup of bubbles into smaller fragments was observed to occur frequently with exposure to higher pressure amplitudes (>580 kPa) in preliminary experiments. Due to the difficulty in analyzing such data on the basis of radius versus time response, the maximum pressure selected for this study was 580 kPa, which was approximately 10% below the threshold for inertial cavitation measured previously for a population of ELIP (640 kPa).

Fragmentation was observed despite operating below the previously measured inertial cavitation threshold for a population of ELIP, although only for a narrow range size range of individual ELIP (0.75-1.05 μm, Table 1) and only for the two highest pressure levels used in this study. The size distribution measured using a Coulter counter indicates that the majority of ELIP particles have radii within this size range, with a volume weighted modal radius of approximately 1 μm, although ELIP suspensions are known to contain particles with a relatively broad size distribution as small as tens of nanometers (Kopechek et al. 2011). The low occurrence of fragmentation is probably due to several factors. First, the pressure applied is lower than the previously measured threshold for ELIP exposed to 6.0-MHz Doppler pulses (640 kPa, Radhakrishnan et al. 2013). Second, the pressure threshold for rapid fragmentation is dependent on the pulse duration, which was fixed at 3.33 μs in this experiment.

The linear resonance radius of ELIP is estimated to be 1.7 μm at 6 MHz based on the viscoelastic shell properties determined in a previous study. Comparing the observations of fragmentation to the linear resonance radius of ELIP suggests that ELIP with radii of approximately one-half the resonant radius are most likely to undergo fragmentation.

However, the resonance frequency and corresponding size is based on the assumption of linear response, which for phospholipid-coated bubbles such as ELIP, is only valid for small expansion ratios ($R_{max}/R_0<1.02$). At larger oscillation amplitudes such as those observed in this study, the interfacial dynamics are also controlled by the free air-water surface tension and the predicted resonance size decreases, approaching a value only slightly larger (10%) than the resonance size of a free bubble (Overvelde et al. 2010). The resonance size of a free air bubble at 6 MHz is 0.5 µm, which is slightly below the size range of ELIP observed to fragment in this study (0.75-1.05 µm). Therefore, our observations are consistent with previous investigations of lipid-shelled UCAs for encapsulated microbubbles with initial radii close to resonance size based on the insonation parameters used in this study.

Surface Modes

Oscillating optical interference patterns indicative of surface mode oscillations were observed were observed in 38% of recordings. Surface mode instabilities are known to be threshold dependent and are readily excitable for bubbles larger than resonance. Moreover, since surface modes are strongly coupled to the pulsation mode, they are normally excited after several acoustic cycles and at lower frequencies than the pulsation mode. Surface mode vibrations may contribute to the observed subharmonic emissions from ELIP at acoustic pressure levels below the inertial cavitation threshold. A subsequent pinch-off or fragmentation of ELIP undergoing surface mode oscillations was not observed. One possible reason is that the acoustic energy drives the surface mode vibrations rather than the volumetric mode oscillations, which results in a lower dilatation rate as observed in this study. Previous studies have shown that a microbubble undergoing surface mode vibrations does not result in lipid shedding, which is a phenomena correlated with acoustically driven diffusion and a corresponding reduction in microbubble size.

ELIP Deflation

Based on the radius versus time response, the deflation process of ELIP was shown to occur in stages rather than continuously, as previously reported for a commercially available UCA microbubble encapsulating OFP gas (Viti et al. 2012). The deflation occurred mostly during the ultrasound exposure—36% of ELIP underwent a size reduction by more than the resolution limit of 0.12 µm within a 3.33 us insonation. Thus the ultrasound mediates the ELIP deflation process during microbubble oscillation.

Gas loss from phospholipid-shelled microbubbles results in a decrease in the encapsulated gas volume, and concomitant reduction in the surface area of the shell. Therefore, less surfactant material is required to stabilize the deflated gas core and excess lipids are expelled during deflation, a phenomena known as lipid shedding. Borden et al. (2005) described a progression of lipid shedding processes for microbubbles undergoing acoustically-driven dissolution due to short pulse acoustic excitations. Briefly, the lipid-shedding process was thought to be composed of (a) expulsion of diffuse, sub-micron vesicles (such as micelles) and (b) build-up and eventual detachment of globular aggregates of shell material after several successive pulses. Later studies based on high-speed fluorescence imaging for microbubbles exposed to longer burst excitations revealed the detachment of lipid particles within a few acoustic cycles and the subsequent transport process of the particles by the surrounding streaming flow field.

Direct optical tracking by high-speed imaging is a convenient method to characterize the evolution of ELIP acoustic responses under consecutive ultrasound tone bursts. The results of this study suggest that the oscillation dynamics of ELIP undergo irreversible changes during deflation. Depending on the acoustic pressure, ELIP with initial radii slightly larger than resonance (1-2 µm) may be caused to deflate during excitation by a long ultrasound tone burst. During subsequent tone bursts, the amplitude of oscillation will increase as the bubble further deflates through the resonance size (1 µm in radius). Therefore, ultrasound tone bursts at pressure amplitudes below the threshold for rapid fragmentation can be used to promote acoustically driven diffusion and affect the controlled dissolution of ELIP. This strategy may be important for the controlled delivery of gas to vascular tissue beds.

Earlier acoustic studies on lipid shelled microbubbles have demonstrated enhancement of peak backscattered intensity shortly after bubble disruption. Possible explanations for this phenomena included the liberation of free gas bubbles from the lipid encapsulation or the transition of dissolving encapsulated bubbles through their resonant size. Later studies on single microbubbles based on both acoustical and optical methods have confirmed the latter assumption, and suggested that dissolving bubbles behave as if they were acoustically excited for the first time (Guidi et al. 2010; Thomas et al. 2012). This same reasoning can be applied to the evolution of oscillation dynamics of a deflating ELIP—it is the instantaneous size rather than the initial size of the ELIP that strongly influences the acoustic response.

Implications for Ultrasound-Enhanced Gas Release from ELIP

These results suggest that two parameters should be carefully considered in order to trigger release of an encapsulated gas with ultrasound pulses. First, the acoustic pressure should be sufficient to initiate the fast deflation of ELIP. If inertial cavitation is to be avoided, peak pressure amplitude of 250 kPa is a reasonable choice. Second, the size distribution of ELIP may significantly influence the duration and temporal release profile of the encapsulated gas. ELIP near resonance size (1 um) will generate a larger instantaneous response to acoustic excitation, which will likely decay over time. However, a higher proportion of larger ELIP particles within a population (>2 µm in radius) may be preferable for theragnostic use. Larger microbubbles scatter ultrasound effectively in the diagnostic frequency range and are a less likely to undergo acoustically driven diffusion or rapid fragmentation due to individual sub-threshold ultrasound tone bursts. Larger encapsulated gas bubbles can be used to deliver a much higher payload because the volume is proportional to the third power of the radius. The agent may achieve maximum efficacy at a later stage when passing through the resonance size due to static dissolution in the circulation.

For controlled delivery of encapsulated gas via ELIP, the acoustically driven diffusion mechanism may be preferable to avoid negative bioeffects associated with inertial cavitation.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. Methods can include a step of providing a subject suffering from cardiovascular disease, a step of diagnosing a subject as having cardiovascular disease, and/or a step of selecting a subject for which an inventive product or method would be suitable.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein. For example, any lipid shell or encapsulated gas component ingredient, etc., can be explicitly excluded. Applicants reserve the right to proviso out of the claims any specific component, component category, or combination thereof, whether or not such component, category, or combination thereof, is recited herein. To the extent, if any, that a echogenic liposome that is known or described in the prior art may include nitric oxide, the instant invention may be distinguished from such prior art liposome or methods utilizing such prior art liposome in, for example, any one or more of the following ways: (i) the echogenic liposomes of the invention comprises one or more gases or lipid shell components not present in the prior art echogenic liposome; (ii) the echogenic liposome of the invention comprises a different amount of specific components, or a specific ratio of specific components, not recognized or appreciated as significant to utility or efficacy in the prior art echogenic liposome and methods; or (iii) the echogenic liposome or methods of the invention omit at least one ingredient present and considered necessary in the prior art liposomes or methods.

What is claimed:

1. A microbubble comprising an at least partially pegylated phospholipid shell, encapsulated nitric oxide, and encapsulated perfluorocarbon of the formula $C_xF_y$, wherein X is 3 and Y is 8, wherein the ratio of NO to $C_xF_y$ is about 1:1 or about 1:9 by volume.

2. The microbubble according to claim 1, wherein the at least partially pegylated phospholipid shell comprises dipalmitoylphosphatidylcholine (DPPC), 1,2-dioleoyl-3-trimethylammonium-propane (DOTAP), 1,2-distearoyl-sn-glycero-3-phosphoethanolamine-N-[methoxy(polyethylene glycol)-2000] (DSPE-PEG2000), and 1,2-distearoyl-sn-glycero-3-phosphoethanolamine-N-[methoxy(polyethylene glycol)-750] (DSPE-PEG750) in a molar ratio of 79:15:3:3.

3. A method of manufacturing the microbubble according to claim 1, the method comprising:
    providing an emulsion comprising phospholipids;
    injecting a volume ratio of nitric oxide and $C_3F_8$ into the emulsion;
    agitating the emulsion; and
    adjusting the temperature of the emulsion to room temperature, wherein freezing of the emulsion is avoided, wherein at least some of the phospholipids are pegylated, wherein the volume ratio of nitric oxide and the perfluorocarbon is about 1:1 or about 1:9.

4. The method according to claim 3 wherein the phospholipids consist of one or more of nonionic and anionic phospholipids.

5. A method comprising administering the composition of claim 1 to a patient.

6. The method of claim 5, wherein the patient suffers from cardiovascular disease.

* * * * *

UNITED STATES PATENT AND TRADEMARK OFFICE
CERTIFICATE OF CORRECTION

| | |
|---|---|
| PATENT NO. | : 10,500,227 B2 |
| APPLICATION NO. | : 14/957705 |
| DATED | : December 10, 2019 |
| INVENTOR(S) | : Christy Holland et al. |

It is certified that error appears in the above-identified patent and that said Letters Patent is hereby corrected as shown below:

In the Specification

At Column 1, Lines 15-19, delete the entire paragraph and substitute therefor:
--This invention was made with government support under HL074002 awarded by the National Institutes of Health. The government has certain rights in the invention.--

Signed and Sealed this
Thirtieth Day of April, 2024

Katherine Kelly Vidal
*Director of the United States Patent and Trademark Office*